US008415166B2

United States Patent
Naaman et al.

(10) Patent No.: US 8,415,166 B2
(45) Date of Patent: Apr. 9, 2013

(54) SEMICONDUCTOR DETECTOR FOR PEROXIDE-BASED EXPLOSIVES

(75) Inventors: Ron Naaman, Yarkona (IL); Eyal Capua, Rehovot (IL); Roberto Cao, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 13/055,287

(22) PCT Filed: May 12, 2009

(86) PCT No.: PCT/IL2009/000477
§ 371 (c)(1),
(2), (4) Date: Jan. 21, 2011

(87) PCT Pub. No.: WO2010/010547
PCT Pub. Date: Jan. 28, 2010

(65) Prior Publication Data
US 2011/0129937 A1    Jun. 2, 2011

Related U.S. Application Data

(60) Provisional application No. 61/082,400, filed on Jul. 21, 2008.

(51) Int. Cl.
*G01N 33/22* (2006.01)
*H01L 29/66* (2006.01)

(52) U.S. Cl.
USPC ............... 436/93; 436/94; 436/103; 436/118; 436/127; 436/130; 436/131; 436/132; 436/133; 436/134; 436/135; 436/136; 436/119; 436/149; 436/151; 422/82.01; 422/82.02; 422/83; 422/88; 422/98; 257/253; 257/414; 257/E29.166

(58) Field of Classification Search .................... 436/93, 436/94, 106, 116, 118, 127, 129, 130, 131, 436/132, 133, 134, 135, 136, 119, 149, 151, 436/103; 422/68.1, 82.01, 82.02, 83, 88, 422/90, 98; 257/40, 194, 253, 414, E29.166
See application file for complete search history.

(56) References Cited

U.S. PATENT DOCUMENTS 6,316,268 B1    11/2001    Yang et al.
6,433,356 B1 *    8/2002    Cahen et al. .................... 257/40
(Continued)

FOREIGN PATENT DOCUMENTS

WO    98/19151 A1    5/1998
WO    02/057738 A2    7/2002
(Continued)

OTHER PUBLICATIONS

Bohrer et al., "Selective Detection of Vapor Phase Hydrogen Peroxide with Phthalocyanine Chemiresistors" J. Am. Chem. Soc., 2008, vol. 130, pp. 3712-3713.

(Continued)

*Primary Examiner* — Maureen Wallenhorst
(74) *Attorney, Agent, or Firm* — Browdy and Neimark, PLLC

(57) ABSTRACT

The present invention provides a device for the detection of a peroxide-based explosive, in particular, triacetone triperoxide (TATP), which is based on a molecular controlled semiconductor resistor (MOCSER) and composed of at least one insulating or semi-insulating layer, at least one conducting semiconductor layer, two conducting pads and a layer of multifunctional organic molecules capable of adsorbing molecules of the peroxide-based explosive. The invention further provides an array of semiconductor devices for the selective detection of a peroxide-based explosive, as well as a method for the selective detection of vapors of a peroxide-based explosive in a gaseous mixture using this array.

21 Claims, 17 Drawing Sheets
(3 of 17 Drawing Sheet(s) Filed in Color)

U.S. PATENT DOCUMENTS

| | | | |
|---|---|---|---|
| 6,767,717 B1 | | 7/2004 | Itzahky et al. |
| 7,118,861 B1* | | 10/2006 | Naaman et al. ............... 435/6.11 |
| 7,129,482 B2 | | 10/2006 | Miller et al. |
| 2004/0072360 A1* | | 4/2004 | Naaman et al. ............... 436/116 |
| 2011/0020944 A1* | | 1/2011 | Waldvogel et al. ............. 436/93 |

FOREIGN PATENT DOCUMENTS

| | | |
|---|---|---|
| WO | 2006/089719 A1 | 8/2006 |
| WO | 2009/017631 A2 | 2/2009 |

OTHER PUBLICATIONS

Camacho et al., "Amperometric Biosensor for Hydrogen Peroxide, Using Supramolecularly Immobilized Horseradish Peroxidase on the B-Cyclodextrin-Coated Gold Electrode" Electroanalysis, 2007, vol. 19, pp. 2538-2542.

Capua et al., "Detection of triacetone triperoxide (TATP) with an array of sensors based on non-specific interactions" Sensors and Actuators, B: Chemical, 2009, vol. 140, pp. 122-127.

Cotte-Rodriguez et al., "Rapid trace detection of triacetone triperoxide (TATP) by complexation reactions during desorption electrospray ionization" Chem. Commun., vol. 2006, pp. 953-955.

Dubnikova et al., "Novel Approach to the Detection of Triacetone Triperoxide (TATP): Its Structure and Its Complexes with Ions" Phys. Chem. A, 2002, vol. 106, pp. 4951-4956.

Gartsman et al., "Molecular control of a GaAs transistor" Chem. Phys. Lett., 1998, vol. 283, pp. 301-306.

Hing-Nin Poon et al., "A quartz crystal microbalance study of p-cyclodextrin self assembly on gold and complexation of immobilized p-cyclodextrin with adamantane derivatives" Journal of Inclusion Phenomena and Macrocyclic Chemistry, 2008, vol. 60, pp. 211-222.

Laine et al., "Electrochemical detection of triacetone triperoxide employing the electrocatalytic reaction of iron(II/III)-ethylenediaminetetraacetate and hydrogen peroxide" Analytica Chimica Acta, 2008, vol. 608, pp. 56-60.

Lu et al., "Highly sensitive electrochemical detection of trace liquid peroxide explosives at a Prussian-blue 'artificial-peroxidase' modified electrode" Analyst, 2006, vol. 131, pp. 1279-1281.

Moore D.S., "Instrumentation for trace detection of high explosives" Rev. Sci. Instrument., 2004, vol. 75(8), pp. 2499-2512.

Pacheco-Londono et al., "Standoff Infrared Detection of Explosives at Laboratory Scale" Proc. SPIE-Int. Soc. Opt. Eng., 2006, 620634/1-620634/8.

Rei et al., "Development of nitric oxide sensor for asthma attack prevention" Mater. Sci. Eng. C, 2006, vol. 26, pp. 253-259.

Singh et al., "Sensors—An effective approach for the detection of explosives" Journal of Hazardous Materials, 2007, vol. 144, pp. 15-28.

Traversa et al., "Sol-Gel Processed $TiO_2$-Based Nano-Sized Powders for Use in Thick-Film Gas Sensors for Atmospheric Pollutant Monitoring" Sol-Gel Sci. Tech., 2001, vol. 22, pp. 167-179.

Vilan et al., "Real-Time Electronic Monitoring of Adsorption Kinetics: Evidence for Two-Site Adsorption Mechanism of Dicarboxylic Acids on GaAs(100)" 1998, vol. 102, pp. 3307-3309.

Wu et al., "Novel NO Biosensor Based on the Surface Derivatization of GaAS by 'Hinged' Iron Porphyrins" Angew. Chem. Int. Ed., 2000, vol. 39, pp. 4496-4500.

\* cited by examiner

SEMICONDUCTOR DETECTOR FOR PEROXIDE-BASED EXPLOSIVES

TECHNICAL FIELD

The present invention relates to detectors for peroxide-based explosives, more specifically to detectors for peroxide-based explosives, based on molecular controlled semiconductor resistors.

BACKGROUND ART

Detection of explosives vapor is a challenge, both in terms of the required sensitivity as well as the selectivity. The need for high sensitivity stems from the very low vapor pressure of many of the explosives and from the requirement of detection at some distance from the vapor source. The selectivity issue arises since most of the explosives are not chemically pure and the detection environment contains vapors of many other chemicals.

A number of analytical techniques are being used in commercial trace detectors, such as ion mobility spectrometry (IMS), electron capture mass spectrometry, surface acoustic waves, chemiluminescence and neutron activation. However, current technologies all have serious analytical shortcomings; in particular, the sensitivity for ambient air analysis is not high enough, and therefore it is necessary to swipe luggage at airports as particulates contain much more of the target compounds. The limitations of current technology are well illustrated by the fact that trained dogs can find hidden explosives and drugs, where detectors cannot. A well-known example of this is searching for landmines. Dogs are indeed about 100 times more sensitive than current detectors, and also excel at discriminating one scent from another.

Under development are sensors that are based on adsorption on surfaces. In addition to the plasmon resonance detection, there is an attempt to develop sensors that are based on quartz micro balance (QMB), which changes its frequency upon adsorption of specific molecules, and electrochemical-based sensors.

The most commercially successful detection method is IMS; however, IMS-based sensors require relatively long sampling time and have a relatively high frequency of false positives.

The state of the art laboratory-based technique for trace analysis is mass spectrometry (MS). In combination with gas chromatography and pre-concentration of analyte during sampling, MS can be as much as 100 times more sensitive than dogs. In MS, analyte molecules are ionized and the ions are separated in a mass analyzer according to their masses. A number of different mass analyzers are being used. The most commonly used ionization method is electron ionization (EI) in which molecules in the gas-phase are bombarded with high-energy electrons. MS owes its remarkable sensitivity to the fact that the efficiency of making ions is high, about 0.01%, and that single ions can be detected. MS owes its ability to reliably identify compounds largely to the highly efficient separation of ions in the mass analyzer. However, GCMS traditionally requires very bulky and expensive instrumentation, as well as long analysis times (for gas chromatography). In the last decade, there has been much progress in making mass spectrometers compact and lightweight enough to be field-deployable, and the most attractive design uses time-of-flight (TOF) mass analyzers. These have the simplest possible construction. They are inherently very sensitive, since they allow for all ions to be detected, and have high resolving power. Unfortunately, TOF analyzers are also very difficult to use with present ionization methods, such as EI, for gaseous compounds. As determined for trinitrotoluene (TNT), the state of the art for MS-TOF detection is less than 105 molecules/cm$^3$.

Peroxide-based explosives, in particular, triacetone triperoxide (TATP) and diacetone diperoxide (DADP), are high-powered explosives that can be easily made using inexpensive, readily available starting materials, which can be purchased in most hardware and paints stores, even in bulk quantities. One class of such peroxide-based explosives can be easily produced by reacting various carbonyl compounds, e.g., ketones, aldehydes and their derivatives, with hydrogen peroxide ($H_2O_2$) under acid catalysis. For example, when a mixture of acetone, $H_2O_2$ and small amounts of a mineral acid such as sulfuric acid is left for several hours at room temperature, white crystals of TATP and DADP are formed. Another commonly used peroxide-based explosive is hexamethylene triperoxide diamine (HMTD), which can be conveniently prepared, e.g., by reacting an aqueous solution of $H_2O_2$ and hexamine in the presence of citric acid or dilute sulfuric acid as a catalyst. HMTD is almost insoluble in water and in common organic solvents at room temperature, and it is too active and unstable to be of commercial use as an explosive.

The vapor pressure of peroxide-based explosives, particularly of TATP, is significantly higher than that of commercial explosives, e.g., $8\times10^{-2}$ torr at 25° C. compared with $6\times10^{-6}$ ton, for TATP and TNT, respectively. However, the detection of peroxide-based explosives is particularly difficult because unlike most of the commercial explosives, all these materials lack nitro groups or any other nitrogen oxide functional groups. Since most of the currently available explosive detectors are based on the detection of nitro groups, they cannot be employed for detection of peroxide-based materials. Unlike many other explosives, TATP cannot be detected by canines. Furthermore, the current IMS-based detection methods are unable to detect TATP since solid particles of TATP evaporate on a very short time.

Various types of detectors for TATP have already been described (Traversa et al., 2001; Moore, 2004; Pacheco-Londono et al., 2006; Lu et al., 2006; U.S. Pat. No. 7,129,482, Bohrer et al., 2008). In some of these detectors, a trace of the material is detected as disclosed in U.S. Pat. No. 6,767,717 or the detection is alternatively performed by complexation reactions during desorption electrospray ionization (DESI) (Cotte-Rodriguez et al., 2006). A theoretical approach has also been suggested, in which TATP forms a complex with adsorbed molecules (Dubnikova et al., 2002). However, it still remains a challenge to devise a detection scheme that provides the ability to detect TATP vapors with a small size detector, at long distances and with a high sensitivity and selectivity, especially towards $H_2O_2$.

International Patent Publication No. WO 98/19151 (corresponding to U.S. Pat. No. 6,433,356) of the same applicant of the present invention, herewith incorporated by reference in its entirety as if fully disclosed herein, describes a hybrid organic-inorganic semiconductor device and sensors based thereon, said device characterized by being composed of: (i) at least one layer of a conducting semiconductor; (ii) at least one insulating layer; (iii) a multifunctional organic sensing molecule directly chemisorbed on one of its surfaces, said multifunctional organic sensing molecule having at least one functional group that binds to the said surface of the electronic device, and at least one other functional group that serves as a sensor; and (iv) two conducting pads on the top layer making electrical contact with the electrically conducting layer, such that electrical current can flow between them at a finite distance from the surface of the device. The semiconductor devices disclosed in WO 98/19151 are referred as molecular controlled semiconductor resistors (MOCSERs) and described as light or chemical sensors.

SUMMARY OF INVENTION

It has been found, in accordance with the present invention, that the molecular controlled semiconductor resistor (MOCSER) concept, previously described (Gartsman et al., 1998; Vilan et al., 1998; Wu et al., 2000; Rei Vilar et al., 2006) and disclosed in the aforesaid WO 98/19151, can be utilized for the development of a small sized hybrid organic-inorganic sensor that is able to detect triacetone triperoxide (TATP)'s vapor with high sensitivity and selectivity. In particular, while the sensitivity is an inherent property of the MOCSER, the selectivity is achieved, in fact, by using an array of MOCSERs, i.e., by combining at least two such devices each coated with a layer of different receptor molecules.

In one aspect, the present invention thus relates to a semiconductor device for the detection of a peroxide-based explosive, said device being composed of at least one insulating or semi-insulating layer, at least one conducting semiconductor layer, two conducting pads, and a layer of multifunctional organic molecules capable of adsorbing molecules of said peroxide-based explosive, wherein said at least one conducting semiconductor layer is on top of one of said insulating or semi-insulating layers, said two conducting pads are on both sides on top of an upper layer which is either one of said conducting semiconductor layers or another of said insulating or semi-insulating layers, making electrical contact with said at least one conducting semiconductor layer, and said layer of multifunctional organic molecules is adsorbed on the surface of said upper layer, between the two conducting pads, wherein exposure of said multifunctional organic molecules to a gaseous mixture containing vapors of said peroxide-based explosive causes a current change through the semiconductor device when a constant electric potential is applied between the two conducting pads.

In another aspect, the present invention relates to an array of semiconductor devices for the selective detection of a peroxide-based explosive, comprising at least one semiconductor device for the detection of a peroxide-based explosive, as defined above, and at least one additional semiconductor device for the detection of a contaminating species selected from the group consisting of CO, $CO_2$, $NO_2$, $O_2$, $N_2$, acetone, ethanol, water and peroxides different from said peroxide-based explosive, said additional semiconductor device being composed of at least one insulating or semi-insulating layer, at least one conducting semiconductor layer optionally oxidized, two conducting pads, and optionally a layer of multifunctional organic molecules capable of adsorbing said contaminating species, wherein said at least one conducting semiconductor layer is on top of one of said insulating or semi-insulating layers, said two conducting pads are on both sides on top of an upper layer which is either one of said conducting semiconductor layers or another of said insulating or semi-insulating layers, making electrical contact with said at least one conducting semiconductor layer, and said layer of multifunctional organic molecules, if present, is adsorbed on the surface of said upper layer, between the two conducting pads, wherein exposure of said upper layer to which said layer of multifunctional organic molecules is optionally adsorbed to a gaseous mixture containing vapors of said contaminating species causes a current change through the additional semiconductor device when a constant electric potential is applied between the two conducting pads.

In a further aspect, the present invention provides a method for the selective detection of vapors of a peroxide-based explosive in a gaseous mixture, said method comprising:
(i) exposing an array of semiconductor devices as defined above to said gaseous mixture; and
(ii) monitoring the presence of said peroxide-based explosive vapors in said gaseous mixture according to the changes in the current measured in said at least one semiconductor device for the detection of said peroxide-based explosive vapors and said at least one additional semiconductor device for the detection of said contaminating species when a constant electric potential is applied between the two conducting pads of each one of said devices.

The peroxide-based explosive of the present invention may be any organic-based peroxide-based explosive material such as triacetone triperoxide (TATP), diacetone diperoxide (DADP) and hexamethylene triperoxide diamine (HMTD), but it is preferably TATP.

BRIEF DESCRIPTION OF DRAWINGS

The patent or application file contains at least one drawing executed in color. Copies of this patent or patent application publication with color drawings will be provided by the Office upon request and payment of the necessary fee.

MODES FOR CARRYING OUT THE INVENTION

Figure 1A:
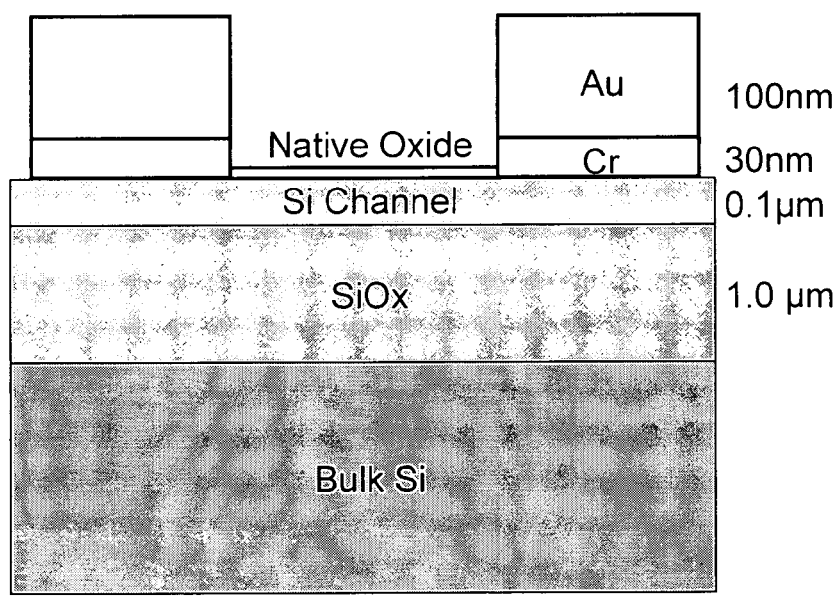
FIGS. 1A-1E show schematic designs of the Si-based MOCSER used in the study described in Example 1 (1A); the GaAs/GaAlAs-based MOCSERs used in the studies described in Examples 1 (1B), 2 (1C) and 3 (1D), respectively; and the die containing 20 devices described in Example 3 (1E).

In one aspect, the present invention relates to a semiconductor device for the detection of a peroxide-based explosive, i.e., to a peroxide-based explosive sensor, being a molecular controlled semiconductor resistor (MOCSER), as defined above.

The semiconductor device of the present invention serves as an amplifier, which translates the peroxide-based explosive vapors concentration on its surface into a change in the electrical current through the semiconductor device when a constant electric potential is applied between the two conducting pads. In particular, due to the adsorption of the analyte molecules, the dipole of the multifunctional organic molecules adsorbed on the surface of the upper layer of the semiconductor device changes, resulting in a change in the resistance of the device followed by a change in the electrical current, as previously described for different molecules (Gartsman et al., 1998; Vilan et al., 1998).

In one embodiment, the semiconductor device of the present invention is composed of at least one insulating or semi-insulating layer, one conducting semiconductor layer, two conducting pads, and a layer of multifunctional organic molecules capable of adsorbing molecules of said peroxide-based explosive, wherein said conducting semiconductor layer is on top of one of said insulating or semi-insulating layers, said two conducting pads are on both sides on top of an upper layer which is either said conducting semiconductor layer or another of said insulating or semi-insulating layers, making electrical contact with said conducting semiconductor layer, and said layer of multifunctional organic molecules is adsorbed on the surface of said upper layer, between the two conducting pads.

The sensing layer in the semiconductor device of the present invention is composed of multifunctional organic molecules capable of adsorbing molecules of the peroxide-based explosive. Non-limiting examples of such multifunctional organic molecules include cyclodextrins, optionally perthiolated or perphosphonated, or compounds of the formula $RPO(OH)_2$, RSH or RCOOH, wherein R is an aliphatic hydrocarbyl optionally interrupted with one or more heteroatoms selected from O, S or N, or containing a functional end-group comprising a heteroatom selected from O, S or N.

Cyclodextrins (CDs) are a family of cyclic oligosaccharides composed of 5 or more α-D-glucopyranoside units linked 1→4, in the $^4C_1$ chair conformation. The most common cyclodextrins have six, seven or eight glucopyranose units and are referred to as α, β and γCD, respectively (Scheme 1 hereinafter). Larger cyclodextrins have also been identified and isolated but have little value in terms of applications (Saenger et al., 1998). As a consequence of their peculiar structure, these molecules feature a conical cavity that is essentially hydrophobic in nature and limited by hydroxyl groups of different chemical characters. The hydroxyl groups located at the narrower side are primary, i.e., come from position 6 of the glucopyranose ring, while those located at the wider entrance are secondary and therefore are less prone to chemical transformation. The reactivity of the hydroxyl groups strongly depends on the reaction conditions. The non-reducing character of cyclodextrins makes them behave as polyols. On the other hand, the large number of hydroxyl groups available implies that careful selection of the reaction conditions is required in order to avoid the substitution of more groups than those needed for a particular purpose.

The inner diameter of the conical cavity in unmodified cyclodextrins varies from 5 to 10 Å and its depth is about 8 Å. For PCDs, the internal and external diameters are about 7.8 Å and 15.3 Å, respectively (Szejtli, 1998), and the calculated surface area is approximately 185 Å$^2$. These dimensions allow the inclusion of several types of guest molecules of appropriate size to form inclusion complexes (Szejtli, 1982). As a consequence of the inclusion, some properties of the guest molecules change, and this phenomenon, in fact, constitutes the basis of practically all cyclodextrin applications, including artificial enzymes, sensors, drug formulations, cosmetics, food technology and textiles (Davis and Brewster, 2004; Szejtli, 1982, 1988 and 1996). Cyclodextrin inclusion complexes can be thermodynamically more or less stable depending on the shape and size of the guest molecule, and the association constants can be measured by a range of physicochemical methods. Absorption and emission spectroscopy along with nuclear magnetic resonance (NMR) and calorimetry are the most popular techniques used to study these systems and have provided an understanding of the structure and energetics of the inclusion process (Connors, 1997). Recently, the use of scanning probe techniques such as atomic force microscopy (AFM) has allowed the measurement of the force involved in these interactions at a single-molecule level (Schönherr et al., 2000; Zapotoczny et al., 2002; Auletta et al., 2004), opening new and exciting prospects in supramolecular chemistry. When a cyclodextrin is considered in the design of a system it is always done to take advantage of its recognition properties to form inclusion complexes.

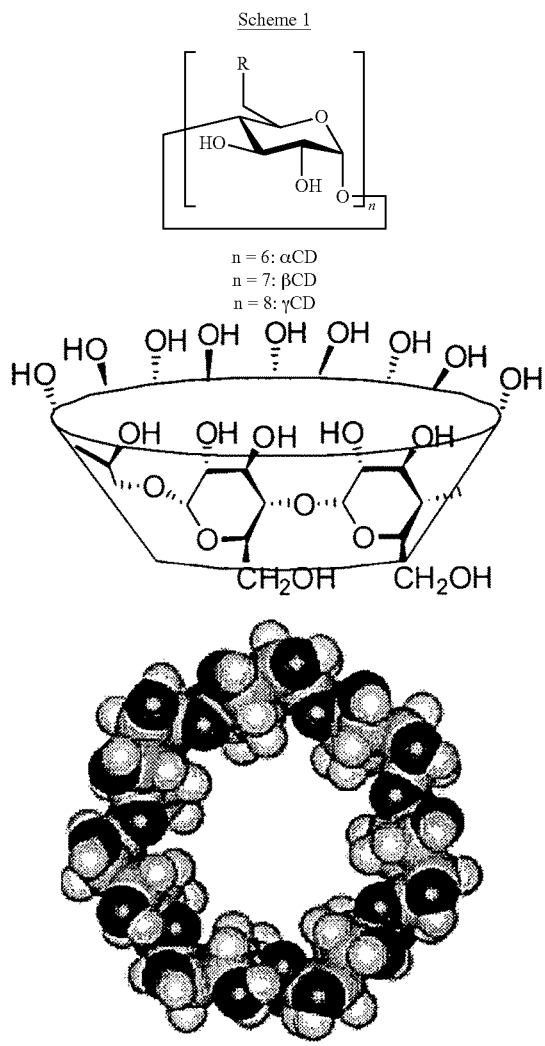

Per-6-thio-β-cyclodextrin (perthiolated βCD), also referred herein as βCDSH, was synthesized as previously described (Rojas et al., 1995). This compound was used to modify gold electrodes and to cap metal, e.g., Au, Ag, Pd and Pt, nanoparticles (Liu et al., 1999, 2000, 2001a, 2001b and 2002; Alvarez et al., 2000; Strimbu et al., 2003), and it can form a uniform and stable self-assembled monolayer on Au. The structure of βCDSH is relatively rigid thus could limit the self-assembly of all seven thiol groups of each molecule. Apparently, only about a half of the thiol groups form Au—S bond. However, if spacer arms are connected between the primary rim and the thiol groups, the flexibility achieved permits a higher participation in the self-assembly (Beulen et al., 2000).

In the case of silicon-silicon oxide substrate, a self-assembled monolayer of thiolated silanes is first formed on the substrate, and the βCDSH molecules are then covalently bonded to the thiolated silanes at a second monolayer (Scheme 2). The binding between the βCDSH and the thiolated silanes is through S—S-bonds.

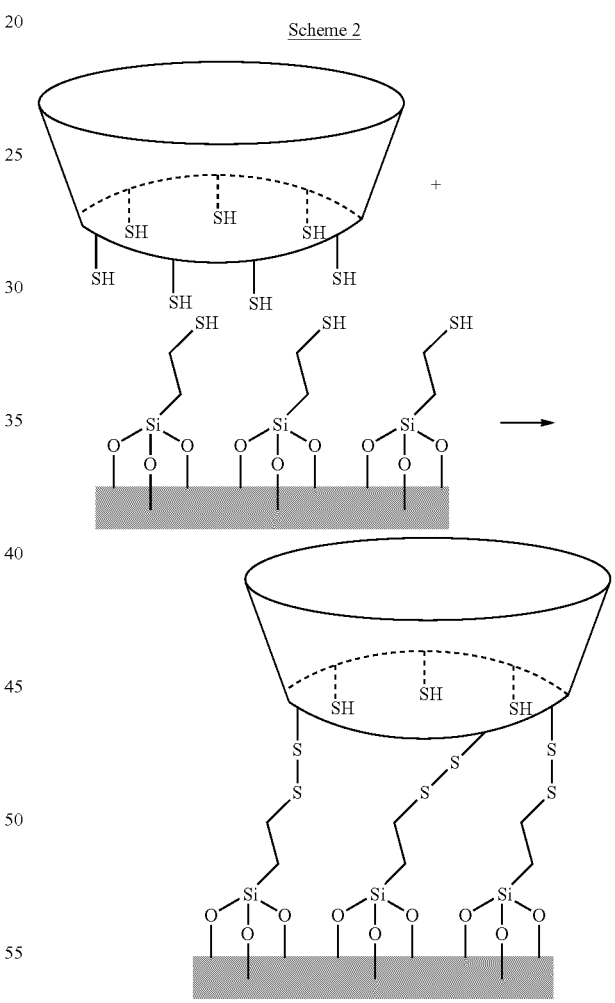

In one embodiment, the multifunctional organic molecule of the present invention is an α-, β- or γ-cyclodextrin, optionally perthiolated or perphosphonated, i.e., an α-, β- or γ-cyclodextrin in which all the hydroxyl groups that come from position 6 of the glucopyranose rings are thiolated or phosphonated. In preferred embodiments, the multifunctional organic molecule is perthiolated α-, β- or γ-cyclodextrin, i.e., per-6-thio-α-, β- or γ-cyclodextrin, more preferably per-6-thio-β-cyclodextrin (βCDSH).

In one embodiment, the cyclodextrin defined above is in the form of an inclusion complex with a hydrophobic guest molecule such as, without being limited to, a cyclic hydrocarbon, capable of removing water molecules adsorbed within the conical cavity of the cyclodextrin, thus enabling the interaction of said cyclodextrin with the vapors of said peroxide-based explosive, e.g., TATP.

The term "cyclic hydrocarbon" as used herein refers to a saturated or unsaturated cyclic molecule containing only carbon and hydrogen atoms and includes $C_3$-$C_{20}$ cycloalkane and $C_3$-$C_{20}$ cycloalkene. The term "$C_3$-$C_{20}$ cycloalkane" typically means a mono-, bi- or tricyclic hydrocarbon having 3-20 carbon atoms and includes, e.g., cyclopropane, cyclobutane, cyclopentane, cyclohexane, cyclooctane, cyclodecane, cycloundecane, cyclododecane, cyclotridecane, cyclotetradecane, cyclopentadecane, cyclohexadecane, cycloheptadecane, cyclooctadecane, cyclononadecane, cycloicosane, bicyclo[3.2.1]octane, bicycle [2.2.1]heptane, adamantane (tricyclo[3.3.1.1$^{3,7}$]decane), bicyclo[2.2.2]octane, decalin (bicyclo[4.4.0]decane), bicyclo[3.3.1]nonane, bicyclo[4.2.2]decane, octahydro-1H-indene, octa-hydropentalene, and the like. Preferred cycloalkane is adamantane, which is the most stable isomer of $C_{10}H_{16}$. Similarly, the term "$C_3$-$C_{20}$ cycloalkene" means a mono-, bi- or tricyclic hydrocarbon having 3-20 carbon atoms and at least one non-aromatic C—C double bond, and includes, e.g., cyclopropene, cyclobutene, cyclopentene, cyclohexene, cycloheptene, cyclooctene, cyclodecene, cycloun-decene, cyclododecene, cyclotridecene, cyclotetradecene, cyclopenta-decene, cyclohexadecene, cycloheptadecene, cyclooctadecene, cyclononadecene, cycloicosene, 1,3-cycloheptene, 1,4-cyclohexadiene, 1,5-cyclooctadiene, and the like.

In a most preferred embodiment, the cyclodextrin of the present invention is an inclusion complex of PCDSH with adamantane, also referred herein as Ada@βCD.

In another embodiment, the multifunctional organic molecule is a compound of the formula RPO(OH)$_2$, RSH or RCOOH, wherein R is an aliphatic hydrocarbyl, optionally interrupted with a heteroatom selected from O, S or N, or containing a functional end-group comprising a heteroatom selected from O, S or N.

The term "aliphatic hydrocarbyl" as used herein refers to an aliphatic radical containing only carbon and hydrogen atoms that may be saturated or unsaturated, linear or branched, and includes $C_2$-$C_{30}$ alkyl, $C_2$-$C_{30}$ alkenyl and $C_2$-$C_{30}$ alkynyl. The term "$C_2$-$C_{30}$ alkyl" typically means a straight or branched hydrocarbon radical having 2-30 carbon atoms and includes, e.g., ethyl, n-propyl, isopropyl, n-butyl, sec-butyl, isobutyl, tert-butyl, n-pentyl, 2,2-dimethylpropyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, icosyl, and the like. Preferred are $C_6$-$C_{22}$ alkyl groups, most preferably $C_9$-$C_{18}$ alkyl groups. The terms "$C_1$-$C_{30}$ alkenyl" and "$C_1$-$C_{30}$ alkynyl" typically mean straight or branched hydrocarbon radicals having 2-30 carbon atoms and 1 double or triple bond, respectively, and include ethenyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, icosenyl, 3-buten-1-yl, 2-ethenylbutyl, 3-octen-1-yl, and the like, and propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, icosynyl, 2-butyn-1-yl, 3-pentyn-1-yl, and the like. Preferred are $C_6$-$C_{22}$ alkenyl or alkynyl groups, most preferably $C_9$-$C_{18}$ alkenyl or alkynyl groups.

In one preferred embodiment, the multifunctional organic molecule of the present invention is a compound of the formula RPO(OH)$_2$, wherein R is a linear $C_6$-$C_{22}$, preferably $C_9$-$C_{18}$, alkyl, optionally interrupted with a heteroatom selected from O, S or N, preferably an oxygen atom, or containing a functional end-group comprising a heteroatom selected from O, S or N. More preferred examples of such molecules include, without being limited to, 1-hexanephosphonate, 9-methoxynonanephosphonate, 11-methoxyundecanephosphonate and 1-octadecane phosphonate, most preferably 1-octadecanephosphonate.

In another preferred embodiment, the multifunctional organic molecule of the present invention is a compound of the formula RSH, wherein R is a linear $C_6$-$C_{22}$, preferably $C_9$-$C_{18}$, alkyl, optionally interrupted with a heteroatom selected from O, S or N, or containing a functional end-group comprising a heteroatom selected from O, S or N. More preferred examples of such molecules include, without being limited to, 11-mercapto-1-undecanol or 1,9-nonanedithiol.

In a further preferred embodiment, the multifunctional organic molecule of the present invention is a compound of the formula RCOOH, wherein R is a linear $C_6$-$C_{22}$, preferably $C_9$-$C_{18}$, alkyl, optionally interrupted with a heteroatom selected from O, S or N, or containing a functional end-group comprising a heteroatom selected from O, S or N.

The various conducting semiconductor and the insulating or semi-insulating layers of the semiconductor device of the present invention are defined as in the basic MOCSER disclosed in the aforesaid WO 98/19151.

In one embodiment, each one of the conducting semiconductor layers in the semiconductor device of the present invention is a semiconductor selected from a III-V and a II-VI material, or mixtures thereof, wherein III, V, II and VI denote the Periodic Table elements III=Ga, In; V=As, P; II=Cd, Zn; VI=S, Se, Te. In preferred embodiments, each one of the conducting semiconductor layers is doped GaAs or doped (Al,Ga)As.

In one embodiment, each one of the insulating or semi-insulating layers in the semiconductor device of the present invention is a dielectric material selected from silicon oxide, silicon nitride or an undoped semiconductor selected from a III-V and a II-VI material, or mixtures thereof, wherein III, V, II and VI denote the Periodic Table elements III=Ga, In; V=As, P; II=Cd, Zn; VI=S, Se, Te. In preferred embodiments, the undoped semiconductor is undoped GaAs or undoped (Al,Ga)As.

Example 1 hereinafter shows the sensitivity of both silicon (Si)- and GaAs-based semiconductor devices to TATP vapors as well as to acetone and ethanol, i.e., contaminating species that may further be found in a gaseous mixture containing TATP vapors. The various receptor molecules used were βCDSH, Ada@βCD, octyltrimethoxysilane, trimethoxysilane and (3-mercaptopropyl)trimethoxysilane. As shown, whereas the Si-based devices responded to acetone and ethanol vapors, a very weak response to TATP vapors was detected in the device coated with Ada@βCD only. Contrary to that, the GaAs-based device showed a high sensitivity to TATP vapors. In particular, while the current through the semiconductor device slightly increased in response to acetone vapors and was absolutely not affected by ethanol vapors, it significantly decreased in response to TATP vapors and was restored to its original value when the vapors flow was turned off. Moreover, the sensitivity of various GaAs-based devices having different length of conducting channel, i.e., different distances between the source and the drain, was about the same, indicating that the signal is proportional to the change in the charge carrier density that is independent of the channel length. This finding is of major importance since it implies that miniaturization of the device does not result in reduced sensitivity. As further shown, while the GaAs-based device coated with Ada@βCD was very sensitive to TATP vapors, the same device was insensitive to hydrogen peroxide ($H_2O_2$), which is the simplest analog of TATP. It is postulated that the enhanced sensitivity of βCDSH to TATP upon inclusion of adamantane is associated with the removal of the water molecules adsorbed in the βCDSH cavity, which enables the interaction of the latter with TATP.

Example 2 shows both the sensitivity and selectivity of GaAs-based devices, coated with various alkanephosphonate receptors, in particular, 1-hexane phosphonate, 11-methoxyundecanephosphonate and 1-octadecanephosphonate, to TATP vapors vs. $H_2O_2$. As shown, the sensitivity to TATP of all the devices examined was at the level of 1 ppm or less, wherein the most sensitive device was that coated with the 1-octadecanephosphonate, which was able to detect TATP vapors at concentrations lower than 0.5 ppm. The time dependency of the signals obtained for the various devices examined indicates that both the length of the alkanephosphonate chain and the polarity of the terminal group thereof are factors affecting the intensity of the signal. Contact potential difference (CPD) studies have further indicated that the sensitivity of the device to TATP inversely correlates with the surface work function, i.e., with a positive charging of the tail group in the receptor molecules, suggesting that upon adsorption of TATP onto the monolayer, and due to its high electron affinity, charge is transferred from the device to the TATP. Specifically, in cases the receptor molecules monolayer is poor in electrons, i.e., relatively positively charged, electrons are transferred from the GaAs-based semiconductor device, causing a decrease in the current as a result of reduction in the number of charge carriers in the conducting channel, whereas in cases the monolayer is electron rich, i.e., relatively negatively charged, electrons are transferred from the monolayer to the TATP without affecting the density of the charge carriers in the GaAs-based device.

The various GaAs-based devices used in the study described in Example 2 did not respond to acetone or ethanol; however, they did respond to $H_2O_2$. Nevertheless, as particularly shown with the GaAs-based device coated with 1-octadecanephosphonate, whereas a similar signal was obtained following the first exposure to TATP vapors or $H_2O_2$, upon consecutive exposures, the signal obtained for TATP remained about the same while the signal obtained for $H_2O_2$ decreased by a factor of four. This GaAs-based device was then combined with a bare superficially oxidized GaAs-based sensor, and as shown, after full oxidation of the GaAs surface, the bare device responded only to $H_2O_2$ and was not affected by TATP. Hence, by combining two devices, one coated with 1-octadecane-phosphonate and the other coated with an oxidized GaAs surface, it was possible to distinguish between TATP and $H_2O_2$ even when the ratio between them was as high as $1:10^4$, i.e., it was possible to detect TATP even in the presence of $H_2O_2$.

Example 3 describes a study in which an array of semiconductor devices consisting of GaAs-based devices each coated with a different monolayer, in particular, 1-hexanephosphonate, 11-methoxy undecanephosphonate, 1-octadecane phosphonate, 11-mercapto-1-undecanol or 1,9-nonanedithiol, as well as a bare GaAs structure superficially oxidized, was exposed to vapors of TATP, $H_2O_2$, acetone or ethanol. As clearly shown, the concept of array-based sensing enabled to distinguishe between TATP and other molecules that may exist in the ambient air, including peroxides other than TATP. As particularly shown, the GaAs-based device coated with 1-octadecane phosphonate was able to detect vapors of TATP at a concentration below 100 ppb, when electrical noise was the main limit to the sensitivity, while the presence of $H_2O_2$ in the gaseous mixture hardly interfered with the sensitivity of this device towards TATP.

FIGS. 1A-1D show schematic designs of the Si-based MOCSER used in the study described in Example 1 (1A), and of the GaAs-based MOCSERs used in the studies described in Examples 1 (1B), 2 (1C) and 3 (1D), respectively.

Thus, in one preferred embodiment, the semiconductor device of the present invention is composed of a first insulating layer of undoped GaAs which is on top of a second insulating layer of undoped GaAlAs, said second insulating layer is on top of a third insulaing layer of undoped GaAs which is on top of a fourth insulating layer of undoped GaAlAs, said fourth insulating layer is on top of a conducting semiconductor layer of GaAlAs which is on top of a fifth insulating layer of undoped GaAs that is on top of a sixth insulating layer of GaAs, wherein on top of said first insulating layer is a conducting semiconductor layer of GaAs on top of which is an upper conducting semiconductor layer of GaAs, and said layer of multifunctional organic molecules capable of adsorbing TATP is adsorbed to said upper conducting semiconductor layer. This configuration is the one represented by FIG. 1B.

In another preferred embodiment, the semiconductor device of the present invention is composed of a first insulating layer of GaAs which is on top of a second insulating layer of undoped GaAlAs, said second insulating layer is on top of a conducting semiconductor layer of GaAs which is on top of a third insulaing layer of undoped GaAlAs, said third insulating layer is on top of a fourth insulating layer of undoped InGaAs which is on top of a fifth insulating layer of undoped GaAs, said fifth insulating layer is on top of a sixth insulating layer of undoped GaAlAs/GaAs which is on top of a seventh insulating layer of undoped GaAs, said seventh insulating layer is on top of an eighth insulating layer of undoped GaAlAs which is on top of a conducting semiconductor layer of GaAlAs, said conducting semiconductor layer of GaAlAs is on top of a ninth insulating layer of undoped GaAs which is on top of a tenth insulating layer of GaAs, wherein on top of said first insulating layer is an upper conducting semiconductor layer of GaAs, and said layer of multifunctional organic molecules is adsorbed to said upper conducting semiconductor layer. This configuration is the one represented by FIG. 1C.

In a further preferred embodiment, the semiconductor device of the present invention is composed of a first insulating layer of GaAs which is on top of a second insulating layer of undoped GaAlAs, said second insulating layer is on top of a conducting semiconductor layer of GaAs which is on top of a third insulating layer of undoped GaAlAs, said third insulating layer is on top of fourth insulating layer of undoped InGaAs which is on top of a fifth insulating layer of GaAs, wherein on top of said first insulating layer is an upper conducting semiconductor layer of GaAs, and said layer of multifunctional organic molecules is adsorbed to said upper conducting semiconductor layer. This configuration is the one represented by FIG. 1D.

In view of the studies described in Examples 1-3 and discussed above, in another aspect, the present invention relates to an array of semiconductor devices for the selective detection of a peroxide-based explosive, comprising at least one semiconductor device for the detection of said peroxide-based explosive as defined above, and at least one additional semiconductor device for the detection of a contaminating species selected from the group consisting of $CO$, $CO_2$, $NO_2$, $O_2$, $N_2$, acetone, ethanol, water, and peroxides different from said peroxide-based explosive, said additional semiconductor device being composed of at least one insulating or semi-insulating layer, at least one conducting semiconductor layer optionally oxidized, two conducting pads, and optionally a layer of multifunctional organic molecules capable of adsorbing said contaminating species, wherein said at least one conducting semiconductor layer is on top of one of said insulating or semi-insulating layers, said two conducting pads are on both sides on top of an upper layer which is either one of said conducting semiconductor layers or another of said insulating or semi-insulating layers, making electrical contact with said at least one conducting semiconductor layer, and said layer of multifunctional organic molecules, if present, is adsorbed on the surface of said upper layer, between the two conducting pads, wherein exposure of said upper layer to which said layer of multifunctional organic molecules is optionally adsorbed to a gaseous mixture containing vapors of a peroxide different from TATP or said contaminating species causes a current change through the additional semiconductor device when a constant electric potential is applied between the two conducting pads.

The sensitivity and selectivity of the array of the present invention result from the fact that this array comprises a semiconductor device coated with a tailored receptor molecule for a peroxide-based explosive, e.g., Ada@βCD or a phosphonate such as 1-octadecanephosphonate as exemplified herein, as well as various additional elements capable of detecting vapors of background gases, i.e., contaminating species, Ada@βCD or a phosphonate such as 1-octadecane phosphonate, as exemplified herein.

Each one of the additional semiconductor devices included in the array of semiconductor devices of the present invention may be designed similarly to the semiconductor device for the detection of a peroxide-based explosive defined above, and may be made from the same materials or, alternatively, from other materials described with respect to the basic MOCSER disclosed in WO 98/19151. Each one of the additional semiconductor devices may also be composed, inter alia, of a sole conducting semiconductor layer.

Thus, in one embodiment, the additional semiconductor devices in the array of semiconductor device of the present invention is composed of at least one insulating or semi-insulating layer, one conducting semiconductor layer optionally oxidized, two conducting pads, and optionally a layer of multifunctional organic molecules capable of adsorbing said contaminating species, wherein said conducting semiconductor layer is on top of one of said insulating or semi-insulating layers, said two conducting pads are on both sides on top of an upper layer which is either said conducting semiconductor layer or another of said insulating or semi-insulating layers, making electrical contact with said conducting semiconductor layer, and said layer of multifunctional organic molecules, if present, is adsorbed on the surface of said upper layer, between the two conducting pads.

In order to distinguish between a peroxide-based explosive, e.g., TATP, and background gases, i.e., CO, $CO_2$, $NO_2$, $O_2$, $N_2$, acetone, ethanol and water, different multifunctional organic molecules capable of adsorbing said contaminating species may be used in each one of said at least one additional semiconductor device included in the array of semiconductor devices of the present invention. Such multifunctional organic molecules may be, e.g., various porphyrines adsorbed on GaAs-based MOCSERs. Alternatively, the selectivity can be achieved by adsorbing the same multifunctional organic molecules used for the detection of the peroxide-based explosive on a silicon-based MOCSER instead of on the GaAs-based MOCSER used for the peroxide-based explosive detection.

As described above, a different approach to distinguish between a peroxide-based explosive, e.g., TATP, and a peroxide different from a peroxide-based explosive, e.g., $H_2O_2$, is to use a bare superficially oxidized GaAs-based sensor as one of said at least one additional semiconductor devices.

Thus, in one embodiment, the at least one additional semiconductor device in the array of semiconductor devices of the present invention is composed of at least one insulating or semi-insulating layer, an oxidized conducting semiconductor layer, and two conducting pads, wherein exposure of said oxidized conducting semiconductor layer to a gaseous mixture containing vapors of a peroxide different from said peroxide-based explosive causes a current change through the additional semiconductor device when a constant electric potential is applied between the two conducting pads.

In another embodiment, the at least one additional semiconductor device in the array of semiconductor devices of the present invention is composed of at least one insulating or semi-insulating layer, a conducting semiconductor layer, two conducting pads, and a layer of multifunctional organic molecules capable of adsorbing said contaminating species, wherein exposure of said multifunctional organic molecules to a gaseous mixture containing vapors of said contaminating species causes a current change through the additional semiconductor device when a constant electric potential is applied between the two conducting pads.

In a further aspect, the present invention provides a method for the selective detection of a peroxide-based explosive in a gaseous mixture, said method comprising:
 (i) exposing an array of semiconductor devices as defined above to said gaseous mixture; and
 (ii) monitoring the presence of said peroxide-based explosive vapors in said gaseous mixture according to the changes in the current measured in said at least one semiconductor device for the detection of said peroxide-based explosive vapors and said at least one additional semiconductor device for the detection of said contaminating species when a constant electric potential is applied between the two conducting pads of each one of said devices.

The method of the present application may be used in order to selectively detect vapors of a peroxide-based explosive, preferably TATP, in open spaces as well as in closed spaces such as terminals, e.g., airport, train and bus terminals, shopping centers, public buildings such as theaters and cinemas, and airplanes. Consequently, the gaseous mixture according to the method of the present invention may be atmospheric air or any gaseous mixture found in any of the aforesaid closed spaces.

To summarize, the molecular controlled semiconductor resistor (MOCSER) is highly sensitive to chemical changes on its surface and has a short response-time (Vilan et al., 1998). The molecules adsorbed on the surface of the MOCSER change the surface potential, which affects the resistance of the MOCSER.

Chemically, it is difficult to find a sensing molecule that selectively interacts with some peroxides and not with others. The approach presented herein overcomes this limitation by utilizing the "non-specific interaction" concept. In other words, in the sensor of the present invention, a layer made of multifunctional organic molecules capable of adsorbing molecules of a peroxide-based explosive, e.g., TATP, is adsorbed on the surface of the upper layer of the semiconductor device and serves as the sensing element. Due to the adsorption of the analyte molecules, the dipole of the receptor molecules changes, resulting in a change in the resistance of the device. Previous studies confirmed that the adsorption of less than 1000 analyte molecules is enough to change the current through the device in a measurable amount.

The low number of molecules the sensor of the present invention is able to detect put it ahead of quartz microbalance biosensor (QMB)- and surface acoustic wave (SAW)-based sensors, and it is by far better than ion mobility detectors. Assuming the same air-collection system, the sensitivity expected from this sensor is by one or two orders of magnitude better than any of the available sensors, beside mass-spectrometry-based sensors.

Other advantages of the peroxide-based explosive sensor of the present invention are the fact that a direct electrical signal is obtained, i.e., that the sensing process is directly transformed into an electrical signal with no need for an additional actuator, as well as its small size and ability to operate in a matrix configuration, as to allow selective detection and enable higher detection reliability.

The ability to obtain time-dependent signals enables to quickly extract the signal by monitoring its gradient, e.g., dI/dt vs. time, even after very short exposure times, and to average over several gradients to obtain a better signal-to-noise ratio.

Because of the array concept, each one of the devices in the array could be designed to be selective for a large number of compounds by adding elements to the array.

Applying the array concept, we were able to reach a detection limit of 100 ppb, as compared with about 10 ppb reported using electrochemical methods for detecting liquid TATP (Lu et al., 2006) and 150 ppb by employing an electrocatalytic reaction (Laine et al., 2008). Nevertheless, unlike the electrochemical methods, the array of semiconductor devices of the present invention detects TATP directly from vapor, while oxygen and $H_2O_2$ affect neither the sensitivity nor the selectivity.

Since the sensors of the present invention are based on microelectronic devices, they can be made compact and their manufacturing is inexpensive. Because of the small surface area of the devices, their manufacture requires only minute amounts of chemicals.

The array of sensors described herein is not only capable of detecting TATP with high sensitivity and selectivity, but also points in an interesting direction for developing sensors that are based on an array in which the elements do not chemically interact with the analytes, but instead undergo weaker interactions. Sensing molecules via such interactions is most advantageous because the sensors are thought to have a short recovery time and their lifespan may consequently increase. Within the framework of this study, the devices were repeatedly used up to six months. Despite the non-specific bonding with the gas phase molecules, the new sensor is sensitive, selective, and very small.

The invention will now be illustrated by the following non-limiting Examples.

EXAMPLES

Experimental

Device Preparation (3-Mercaptopropyl)trimethoxysilane, octyltrimethoxysilane, trimethoxy(2-phenylethyl)silane, bicyclohexyl (BCH) and adamantane (Ada), were purchased from Sigma. Per-6-thio-β-cyclodextrin (perthiolated β-cyclodextrin, referred herein as βCDSH) was synthesized as described in Rojas et al., 1995.

Silicon (Si)-based MOCSERs were provided by Intel Research Israel Lab. Prior to silanization, these devices were cleaned by sonication in ethyl acetate (2 min) and were then rinsed with acetone and ethanol. Silanization with mercaptosilane was carried out by immersing the devices in 1 mM mercaptosilane in BCH solution for 180 min in darkness and at room temperature. Silanizations with phenylsilane and octylsilane were carried out for 60 sec in 1 mM silane in BCH. The substrates were then sonicated for 1 min in toluene and kept in Ar. The self-assembly of βCDSH on Si substrates was achieved by immersing the devices in 0.5 mM βCDSH in Milli-Q water (18.2 MΩ) for 200 min. Next, the substrates were washed twice with water followed by two washes in ethanol. The devices were kept in a desiccator until further use. The inclusion of Ada into the β-cyclodextrin (βCD) cavity was carried out in solutions of 10 mM in ethanol for 120 min. The devices were washed twice with ethanol and kept in a desiccator.

GaAs-based MOCSERs were prepared in the laboratory of the present inventors. The self-assembly of βCDSH on GaAs substrates was carried out without using mercaptosilane, particularly, by immersing HF-etched substrates directly in 0.5 mM βCDSH in dry acetonitrile for 200 min and then washing twice with acetonitrile. The deposition of Ada was performed as described for the Si substrates.

Electrical Measurements

All electrical measurements were carried out on wire-bonded devices. Currents through the MOCSERs were measured using a multimeter/switch system Keithley model 2700. Biasing of source-drain and source-backgate was carried out using two Keithley 236 source/measure units. Si-based devices were biased through constant voltages of source-drain and source-backgate. GaAs-based devices were biased only through their source-drain terminal.

The measurements were carried out in a dark chamber with a constant flow of $N_2$ at a rate of 500 cc/min. Exposure of the devices to vapors of acetone, ethanol and TATP was performed only after up to four minutes of stabilization time. The different analytes were evaporated in a 30-ml chamber at room temperature and the vapors were carried by a constant flow of $N_2$ at a rate of 80 cc/min. This stream of nitrogen was combined with the main nitrogen flow downstream and was then introduced to the sensor.

Contact Potential Difference (CPD)

Contact potential difference (CPD) measurements were determined using a commercial Kelvin probe instrument (Delta Phi Besocke, Jülich, Germany) within a Faraday cage in an $N_2$-filled glove box at atmospheric pressure. The reference probe consisted of a gold grid.

Example 1

Si- and GaAs-Based MOCSERs Coated with Cyclodextrins

In this study we measured the sensitivity of both silicon (Si)- and GaAs/GaAlAs-based devices to acetone, ethanol and triacetone triperoxide (TATP) vapors. The various receptor molecules used were perthiolated β-cyclodextrin (βCDSH), PCDSH with inclusion of adamantane (Ada@βCD), octyltrimethoxy silane, trimethoxy(2-phenylethyl)silane and (3-mercaptopropyl)trimethoxysilane. Bare device was used as a control. All the experiments were conducted at 25° C.

In the case of Si-based devices, in which the surface was coated with a layer of silicon oxide, thiolated silane was used as a linker between the receptor molecules and the solid substrate. In the case of GaAs-based devices, the thiolated receptors were self-assembled directly on the surface of the device.

Figure 1B:
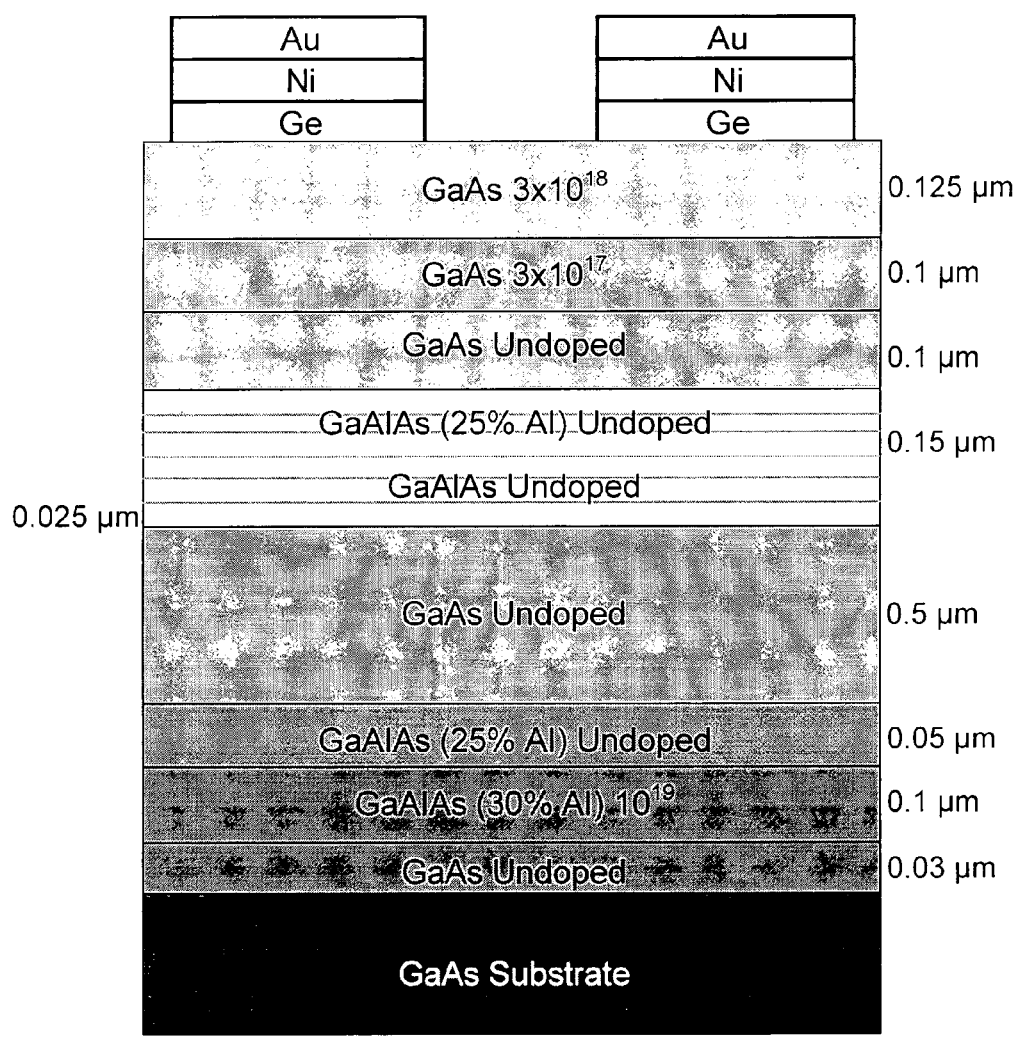
Figure 2A:
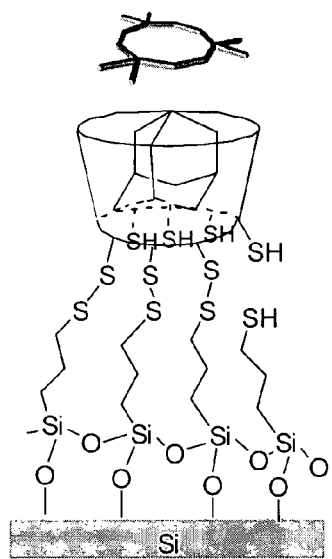
FIGS. 2A-2B schematically show the adsorption of perthiolated β-cyclodextrin (βCDSH) on Si (2A) and GaAs (2B) surfaces, as well as the inclusion of adamantane in the β-cyclodextrin (βCD) cavity and the proposed configuration for the adsorption of TATP to this receptor system.
Figure 2B:
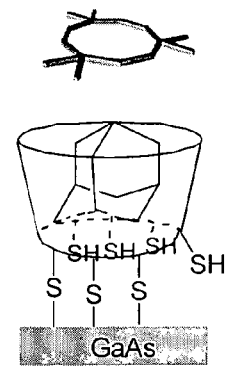

FIGS. 1A-1B show a schematic structure of the Si- and the GaAs-based devices used in this study. In the case of the GaAs-based devices, several distances between the two electrodes were probed, whereas the width of the conductive channel was fixed at 200 μm. In the Si-based devices, the distance between the electrodes was 5 μm. FIG. 2 schematically shows the adsorption of PCDSH on Si and GaAs surfaces, as well as the inclusion of adamantane in the β-cyclodextrin (βCD) cavity and the proposed configuration for the adsorption of TATP to this receptor system. In all Si-based devices, a back-gate voltage was applied and the voltage was optimized as to obtain the maximum response, and it slightly varied from one device to another. No back-gate was used for GaAs-based devices.

Figure 3:
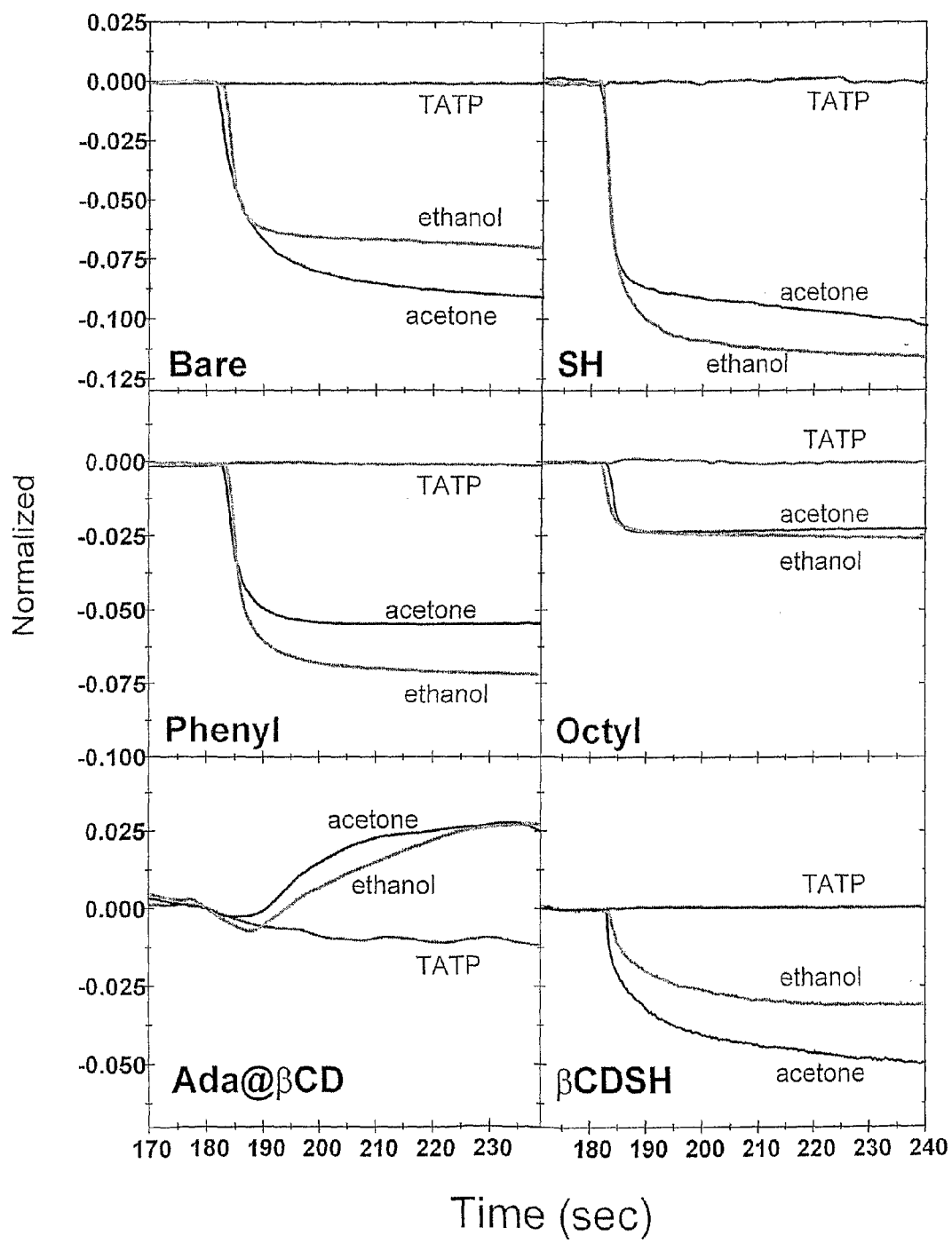
FIG. 3 shows normalized change in the current through Si-based MOCSERs coated with different receptor molecules, as a result of exposure to acetone, ethanol and TATP vapors. The source drain potential during measurements was 1 volt. Bare indicates bare device. SH, Phenyl, Octyl, βCDSH and Ada@βCD indicate (3-mercaptopropyl)trimethoxysilane, trimethoxy(2-phenyl ethyl)silane, octyl-trimethoxysilane, perthiolated β-cyclodextrin and perthiolated β-cyclodextrin with inclusion of adamantane, respectively, as receptor molecules.

Vapors of acetone, ethanol and TATP were mixed with nitrogen flow at a distance of about 20 cm from the sensor, and the response of the Si-based devices was tested. FIG. 3 shows the response of the various Si-based devices to each one of the analytes, expressed by either increasing or decreasing of the current through the device, depending on the specific coating of the device, wherein the response time of each device was due to the time it took for the vapor to reach the sensor. As shown, all the devices responded to acetone and ethanol vapors, whereas only devices coated with Ada@βCD showed a response, in particular, a very weak response, to TATP.

Figure 4:
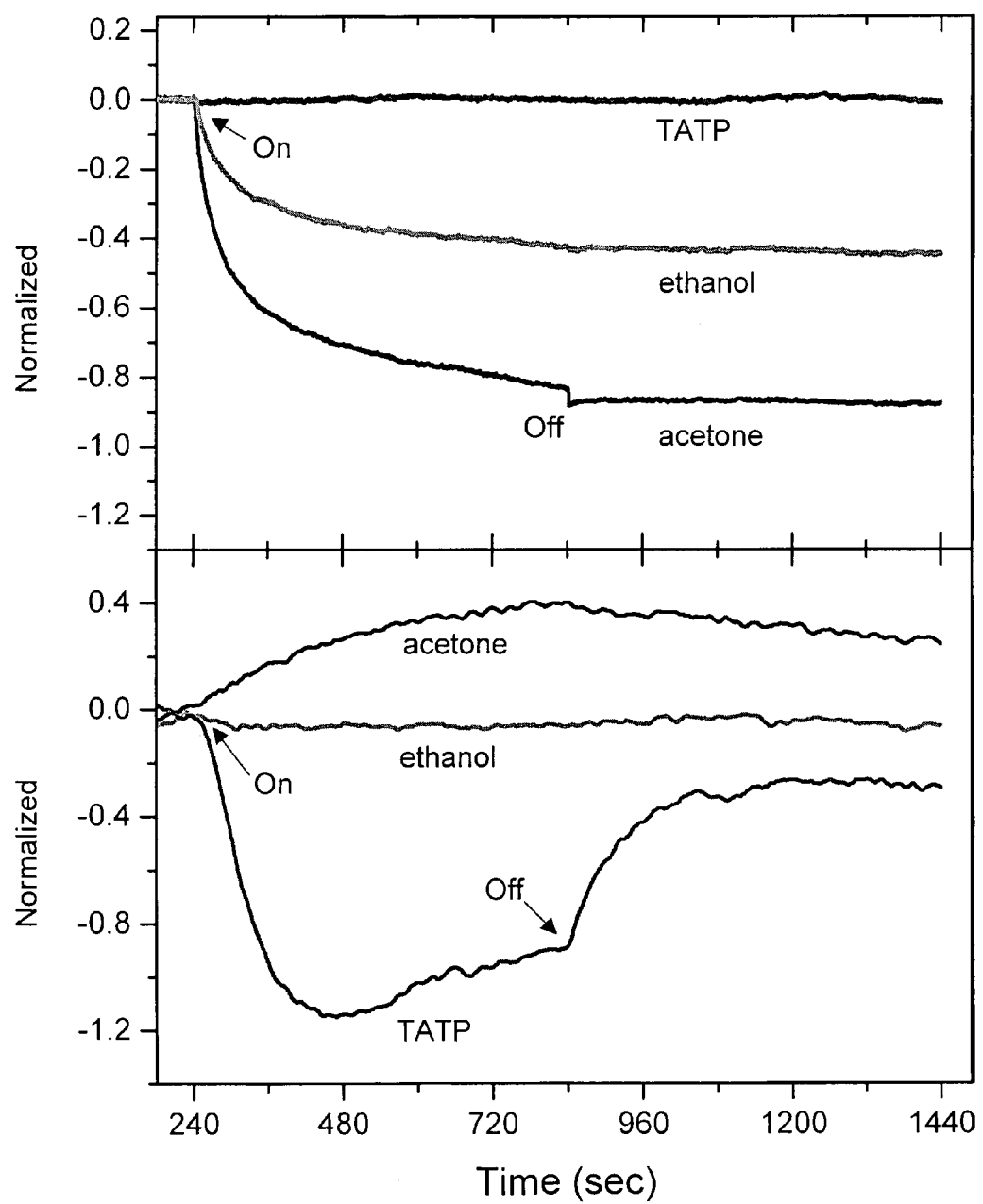
FIG. 4 shows normalized responses of Si-based (upper panel) and GaAs-based (lower panel) MOCSERs coated with Ada@βCD to vapors of acetone, ethanol and TATP, wherein "on" and "off" refer to opening and closing of the vapor flow, respectively.

A similar experiment with the same analytes was then conducted using both Si- and GaAs-based devices coated with Ada@βCD. FIG. 4 shows that whereas the Si-based device responded to ethanol and acetone and exhibited almost no response to TATP, the contrary was true for the GaAs-based device, which was not affected by vapors of ethanol; however, responded with a small increase in current to vapors of acetone, and with a significant decrease in current to vapors of TATP. As further shown, when the vapor flows were turned off, the current was restored almost to its original value.

In the case of the Si-based devices, upon shutting off the flow of nitrogen that carried the analytes' vapors, the current did not return to its base level. Furthermore, additional exposures to the analytes' vapors were not followed by a significant response, as observed following the first exposure, unless in cases in which the back-gate potential was reduced to zero and then raised back, suggesting that once the current varies due to the first exposure to the analyte molecules, the back-gate potential stabilizes the number of charge carriers, which does not change as long as the back-gate voltage is kept constant. When the voltage is reduced, the charge carriers' density is restored back to its original value and the device behaves as a "fresh" device. In the GaAs-based devices however, since no back-gate is used, this effect was not observed.

Figure 5:
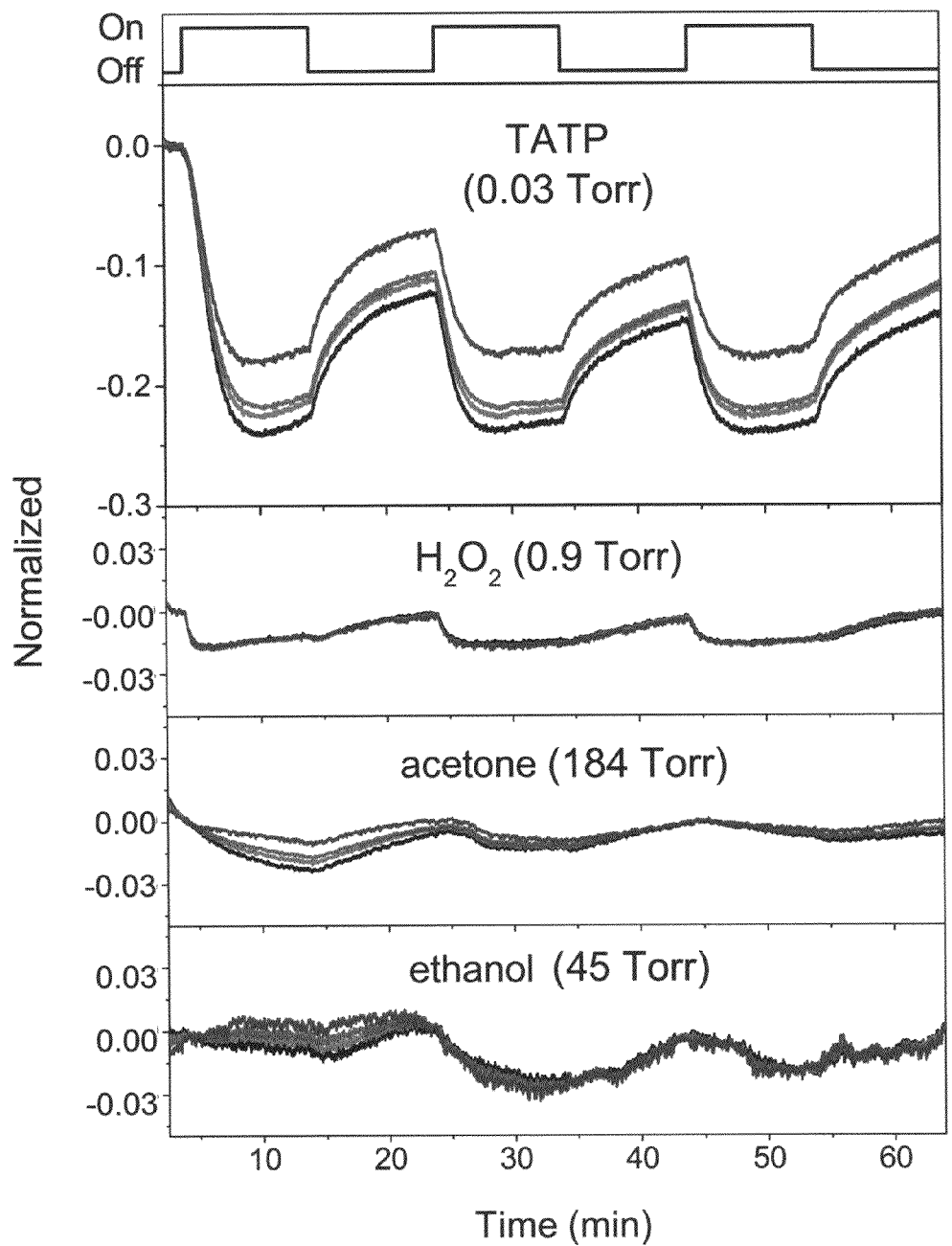
FIG. 5 shows repeated exposures of GaAs-based MOCSERs coated with Ada@βCD to TATP, $H_2O_2$, acetone and ethanol. The exposure to the vapors was performed according to the top diagram, and the different curves referring to each one of the analytes correlate to devices having a different channel length, i.e., distance between the source and drain electrodes, of 2000 (black), 1000 (red), 600 (green) and 200 (blue) μm. The width of the channel in all cases is 200 μm. The vapor pressure at equilibrium (20° C.) of each of the analytes is noted in parentheses.

FIG. 5 shows repeated exposures of GaAs-based devices having the same width but a different length, i.e., distance between the source and the drain, of conducting channel, coated with Ada@βCD, to acetone, ethanol, TATP and hydrogen peroxide ($H_2O_2$), which is the simplest analog of TATP. As interestingly shown, the sensitivity of all the devices was about the same. This is because the signal is proportional to the change in the charge carrier density, and therefore, since the density of the sensing molecules on the surface is independent of the channel length, upon adsorption of the analyte, the change in the charge carrier density was the same for all devices. This finding is of major importance since it implies that miniaturization of the device does not result in reduced sensitivity. The GaAs-based device coated with Ada@βCD was insensitive to $H_2O_2$, despite the high vapor pressure of the latter, indicating the high selectivity of this device to TATP. It is postulated that the enhanced sensitivity of βCDSH to TATP upon inclusion of adamantane is associated with the removal of the water molecules adsorbed in the βCDSH cavity, which enables the interaction of the latter with TATP.

Table 1 summarizes the sensitivity of the Si-based devices coated with various receptor molecules, as well as of the GaAs-based device coated with Ada@βCD as receptor molecules, to acetone, ethanol and TATP, wherein sensitivity is calculated by the percentage of change in the current to one part per million (ppm) of vapor. As shown, the GaAs-based device coated with Ada@βCD exhibited the highest sensitivity to TATP with a detection limit lower than 1 ppm. Si-based devices coated with Ada@βCD responded to TATP but with a much lower sensitivity. The sensitivity to ethanol was found to be the highest for the Si-based device coated with thiolated silane. This array configuration clearly allowed distinguishing among the three substances with a very high selectivity.

TABLE 1

Sensitivity* of Si- and GaAs-based devices to acetone, ethanol and TATP

| Device type | Analyte | | |
|---|---|---|---|
| | Acetone | Ethanol | TATP |
| Si-based | | | |
| Bare | −36 ± 2 | −108 ± 17 | −89 ± 56 |
| SH | −41 ± 2 | −184 ± 21 | 51 ± 86 |
| βCDSH | 10 ± 2 | 32 ± 21 | −116 ± 40 |
| Ada@βCD | −19 ± 3 | −52 ± 1 | 364 ± 98 |
| Phenyl | −22 ± 2 | −114 ± 14 | −147 ± 69 |
| Octyl | −9 ± 1 | −39 ± 8 | 51 ± 92 |
| GaAs-based | | | |
| Ada@βCD | 0.15 ± 0.02 | 0.10 ± 0.04 | −1078 ± 69 |

*The units are $(I_m/I_0 - 1) \times 10^6$ ppm$^{-1}$, wherein $I_0$ and $I_m$ are the current measured before and after exposure to the analyte, respectively. SH, Phenyl, Octyl, βCDSH and Ada@βCD represent (3-mercaptopropyl)trimethoxysilane, trimethoxy (2-phenylethyl) silane, octyltrimethoxysilane, perthiolated β-cyclodextrin, and βCDSH with inclusion of adamantane, respectively. The sign indicates if the current increases or decreases by the analyte.

This study provides an insight into the interaction of adsorbed molecules with semiconductor substrates. In particular, one may expect that the GaAs-based device will be more sensitive relative to the Si-based device, due to the higher mobility of electrons. However, the results of this study indicate that while the GaAs-based device coated with Ada@βCD was more sensitive to TATP compared with the Si-based device coated with the same receptor molecules, it was less sensitive to ethanol and acetone.

Figure 6:
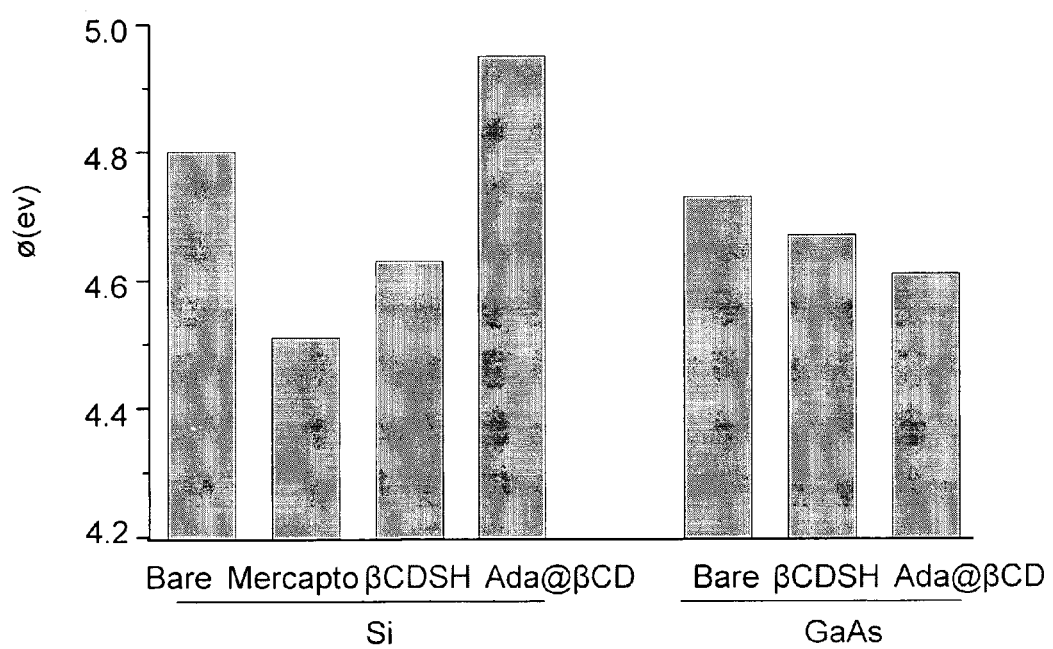
FIG. 6 shows the work functions of GaAs- and Si-based MOCSERs coated with different sensing molecules. As shown, the work function of the GaAs-based device decreased upon attaching the PCDSH or the Ada@βCD, whereas the work function of the Si-based device increased upon attaching the Ada@βCD, indicating that the cyclodextrin, when attached to the GaAs substrate, is positively charged, while when attached to the Si-coated mercaptosilane is negatively charged.

In view of that, the explanation to these findings cannot reside in the coupling of the receptor molecules to the substrate, since if the coupling affects the sensitivity, it should have had the same effect for all analytes. Hence, the difference in the sensitivity of these two devices must be related to the relative position of the energy states of the analyte and the semiconductors. Indeed, contact potential difference (CPD) studies (Vilan et al., 2003; Cohen et al., 1999) showed that in the case of GaAs-based devices, the adsorption of Ada@βCD reduced the work function, indicating that the adsorbate was at least partially positively charged, whereas in the case of Si-based devices, the adsorption of these receptor molecules increased the work function, indicating that the adsorbate was at least partially negatively charged (see FIG. 6).

It is therefore suggested that upon adsorption of TATP to the partially positive Ada@βCD binding system, and due to the high electron affinity of TATP (Liu et al., 2007), electrons are transferred from the GaAs-based device via the positively charged binding system to the TATP, and as a consequence, the number of charge carriers in the device is reduced followed by reduction of the current through the device, as observed experimentally. Since acetone and ethanol have much lower electron affinity, there are not efficient in withdrawing electrons from the GaAs substrate. Contrary to that, in the case of Si-based devices, upon adsorption of TATP to the partially negative Ada@βCD binding system, electrons are transferred from the binding system to the TATP and there is no driving force for withdrawing electrons from the substrate, thus the sensitivity for TATP is low. Similarly, it was recently found that when monoalkylthiols and alkyl dithiols are adsorbed on GaAs, their tail group is positively charged, whereas when adsorbed on gold, it is negatively charged (Aqua et al., 2008).

Example 2

GaAs-Based MOCSERs Coated with Alkanephosphonates

Figure 1C:
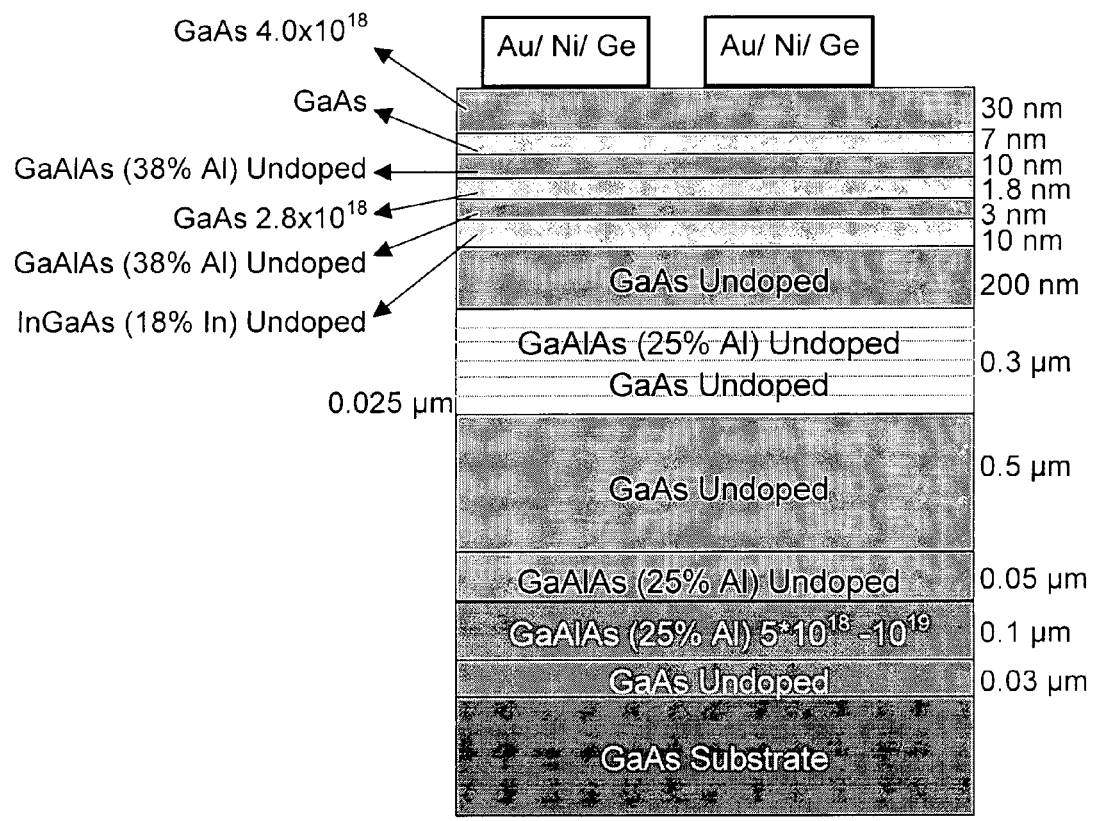

In this study we measured both the sensitivity and the selectivity of GaAs-based device to TATP vapors, as well as to hydrogen peroxide ($H_2O_2$). The semiconductor devices used were GaAs-based devices, as illustrated in FIG. 1C, coated with different alkanephosphonate monolayers that were self-assembled directly on the surface of the device. The specific alkanephosphonate used were 1-hexanephosphonate (C6Phosp), 11-methoxyundecanephosphonate (MeOC11Phosp) and 1-octadecanephosphonate (C18Phosp). As previously found, the phosphonates bind strongly to the GaAs substrate, forming a monolayer coating sufficiently stable in order to prevent surface oxidation (Artzi et al., 2003; Aqua et al., 2007).

Figure 7A:
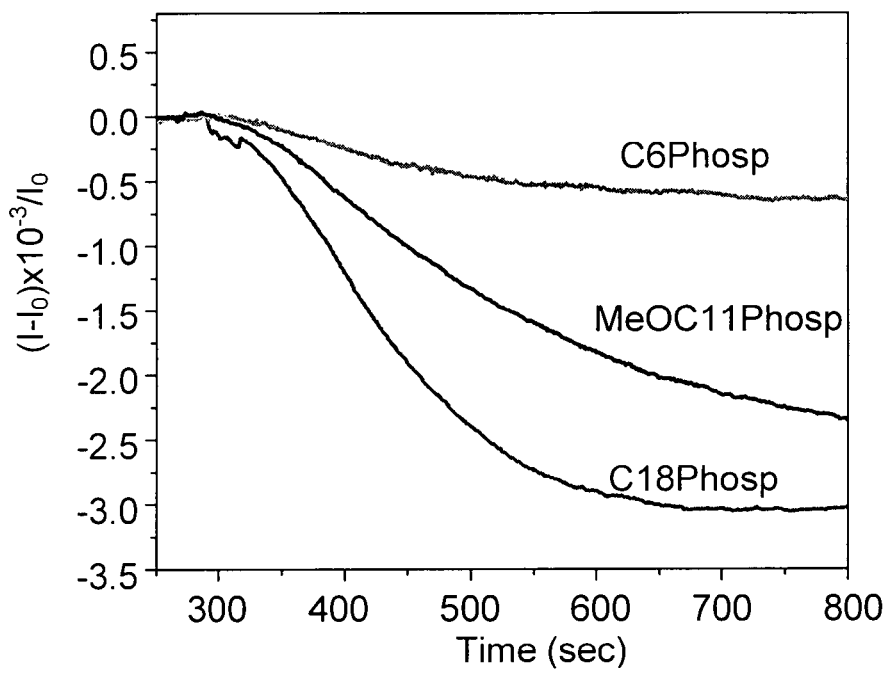
FIGS. 7A-7B show the normalized change $(-(I-I_0)\times 10^{-3}/I_0)$ in the current vs. time for a GaAs-based MOCSER coated with a monolayer made of 1-hexanephosphonate (C6Phosp), 11-methoxyundecanephosphonate (MeOC11Phosp) or 1-octadecanephosphonate (C18Phosp), when exposed to 10 ppm TATP (7A); and the work function (WF) of the different phosphonate systems, calculated according to CPD measurements with respect to the reference gold electrode, wherein the accuracy of the measurements was ±0.005 volt (7B). $I_0$ is the base line current in the device, and I is the current measured following exposure to the vapor.

FIG. 7A shows the signal obtained as a function of time when the various MOCSERs coated with the different alkanephosphonates were exposed to TATP. The observed curves can be characterized by two parameters, i.e., the maximal change in the current as a result of the exposure to TATP and the rate at which the current is changed. The rate observed depends on two parameters, i.e., the diffusion time of the TATP vapors in the gas and the adsorption probability onto the layer. The actual response time of the sensor is several orders of magnitude faster. As clearly shown, the most sensitive device was the one coated with C18Phosp, which was able to detect TATP at concentrations lower than 0.5 ppm. The device coated with MeOC11Phosp had a sensitivity of about 0.7 ppm, and the weakest signal was obtained with C6Phosp, with a sensitivity of 1 ppm. The time dependence of the signals indicates that both the length of the chain and the terminal group polarity are factors that affect the intensity of the signal. For example, MeOC11Phosp monolayer with a chain of 5 atoms longer than that of C6Phosp monolayer presented a sensitivity of about 3.3 times higher than that of the latter; however, a slower response. The chain of MeOC11Phosp, which is 7 atoms shorter than that of C18Phosp, presented a sensitivity of only 1.3 times less than that of the latter.

Figure 7B:
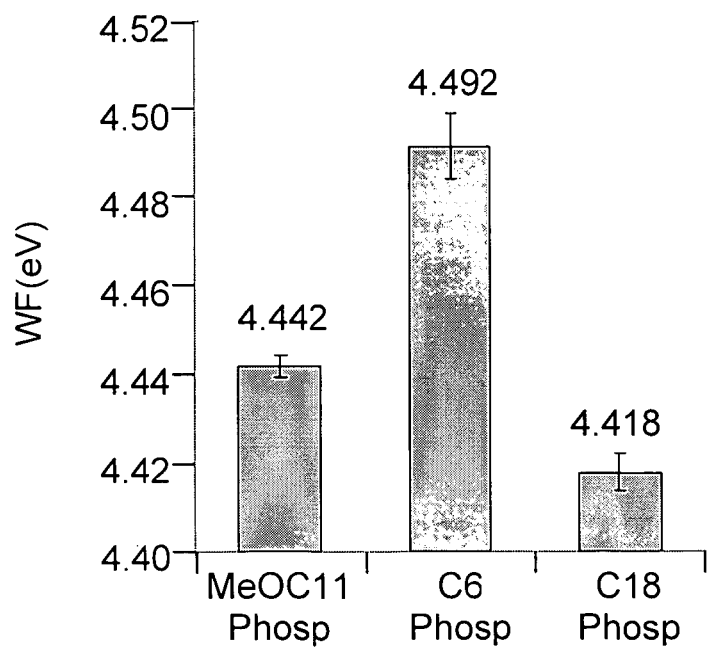

In order to rationalize the variation in the sensitivity, CPD studies were performed, during which the work function of GaAs coated with each one of the monolayers was measured and compared with a reference gold electrode. It was expected that if the tail of the molecules in the monolayer is positively charged relative to the substrate, the work function would be reduced. As shown in FIG. 7B, the sensitivity of the device to TATP inversely correlated with the surface work function, i.e., with a positive charging of the tail group in the monolayer, suggesting that upon adsorption of TATP onto the receptor molecules monolayer, and due to its high electron affinity, charge is transferred from the device to the TATP. If the monolayer is poor in electrons, i.e., positively charged, electrons are transferred from the GaAs-based semiconductor device, causing a decrease in the current as a result of reduction in the number of charge carriers in the conducting channel. However, if the monolayer is electron rich, i.e., negatively charged, electrons are transferred from the organic monolayer to the TATP without affecting the density of the charge carriers in the GaAs-based device.

These findings indicate that the signal measured is not a result of the TATP penetration into the receptor monolayer, since although the monolayer formed by C6Phosp is less organized than those formed by the other phosphonates, thus expected to allow better penetration of adsorbates between the adsorbed molecules, this monolayer showed the longest response time and the lowest signal. Hence, it is concluded that TATP is adsorbed on top of the monolayer as also confirmed by sequential exposing of the sensor to TATP, wherein the recover time of the device was short (see FIG. 8).

Figure 8:
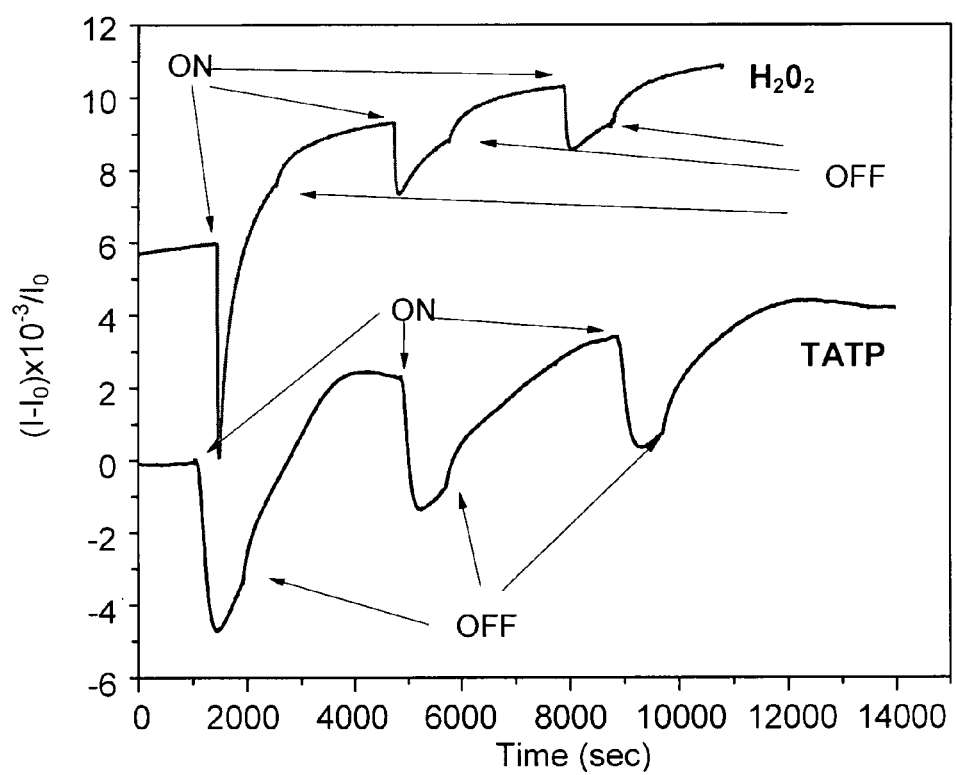
FIG. 8 shows the normalized signal obtained for a GaAs-based MOCSER coated with 1-octadecanephosphonate (C18Phosp) when exposed to 10 ppm TATP or 300 ppm $H_2O_2$ vapors in nitrogen. ON and OFF relate to opening and closing, respectively, of the vapor flow.

In an additional experiment, in which GaAs-based devices, each coated with one of the aforesaid monolayers, were used, it was found that these devices do not respond to acetone or ethanol; however, they do respond to $H_2O_2$, as shown in FIG. 8. The signal observed when the GaAs-based device coated with C18Phosp monolayer was exposed for the first time to these vapors (10 ppm TATP or 300 ppm $H_2O_2$) was about the same for the two compounds, although the response time to $H_2O_2$ was much faster. However, upon consecutive exposures, the signal obtained for TATP remained about the same, while the signal obtained for $H_2O_2$ decreased by a factor of four.

Figure 9:
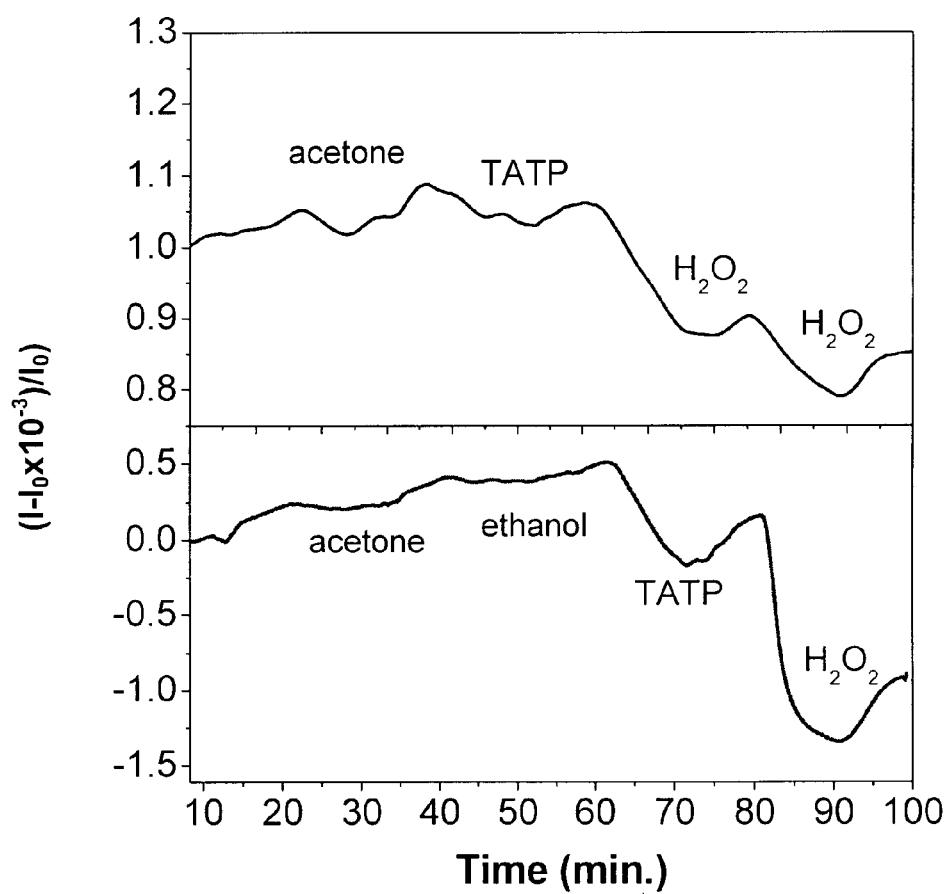
FIG. 9 shows the signal measured for a bare GaAs-based MOCSER partially or fully oxidized (lower and upper graph, respectively), i.e., oxidized for 5 or 10 minutes, respectively, following exposure to TATP, $H_2O_2$, acetone and ethanol.

Since the observed selectivity to $H_2O_2$, which is about 1:600, could not be considered sufficient, the sensor coated with C18Phosp was combined with another sensor, which was a bare superficially oxidized GaAs-based sensor. FIG. 9 shows the results obtained with partially and fully oxidized GaAs surfaces. While the partially oxidized GaAs-based device did not respond to acetone and ethanol, but did respond to both TATP and $H_2O_2$, the fully oxidized GaAs-based device responded only to $H_2O_2$ and was not affected by TATP. Hence, by combining two different devices, one coated with C18Phosp and the other coated with oxidized GaAs surface, it was possible to distinguish between TATP and $H_2O_2$ even when the ratio between the vapor concentrations of these two analytes was as high as $1:10^4$. In other words, by calibration the oxidized device to $H_2O_2$ it was possible to detect TATP even in the presence of $H_2O_2$.

Example 3

An Array of GaAs-Based MOCSERs Each Coated with Different Receptor Molecules

Figure 1D:
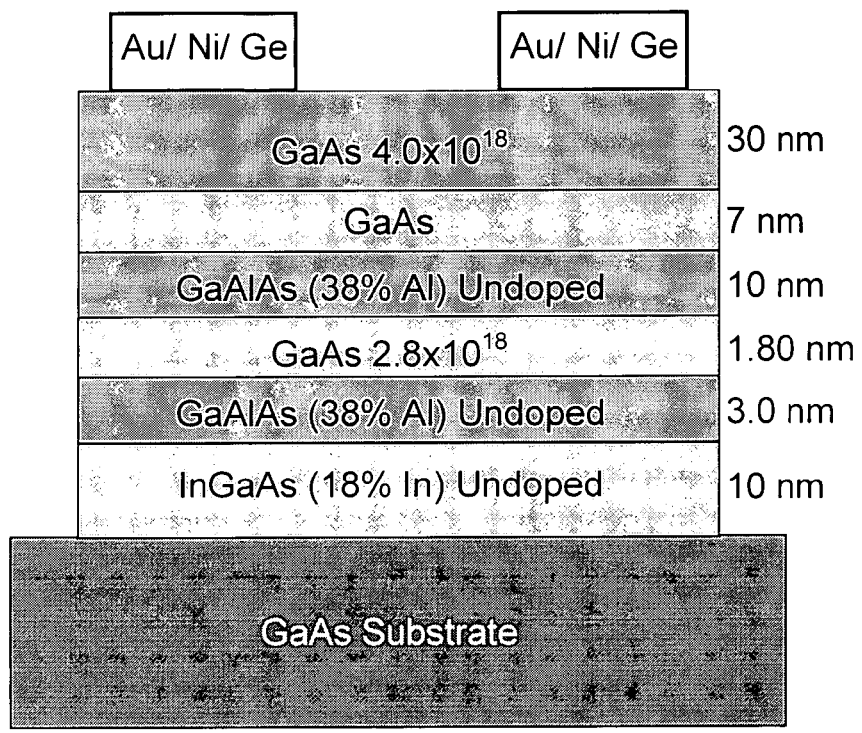

In this study, three phosphonate and two thiol-containing molecules were selected for adsorption as monolayers on the GaAs-based device illustrated in FIG. 1D, in order to explore different anchoring groups, chain lengths and exposed termini. The molecules selected were 1-hexanephosphonate (C6Phosp), 11-methoxy undecanephosphonate (MeOC11Phosp), 1-octadecanephosphonate (C18Phosp), 11-mercapto-1-undecanol (hydroxythiol) and 1,9- nonanedithiol (dithiol). The various organic monolayers were adsorbed and characterized as previously described (Artzi et al., 2003; Aqua et al., 2007). The phosphonates bind strongly to the GaAs substrate, forming a monolayer coating sufficiently stable in order to prevent surface oxidation. This is in contrast to thiols, where the substrate is oxidized underneath the monolayer.

Prior to the adsorption, the devices were sonicated in isopropanol, acetone, and ethanol for 10 min each, followed by UV/ozone oxidation (UVOCS ultraviolet/ozone cleaner) for 10 min. The substrates were etched for 5 sec in 2% HF, rinsed in water, and were then dipped for 30 sec in $NH_4OH$ (about 25% $NH_3$) and rinsed in water again. After drying under $N_2$ stream, the samples were immediately placed in the adsorption solution. Solvents were reagent grade or better. Adsorption was carried out overnight in $N_2$-filled vials placed in a desiccator. After adsorption, the samples were rinsed with tetrahydrofuran or methanol and dried with N, flow.

Figure 1E:
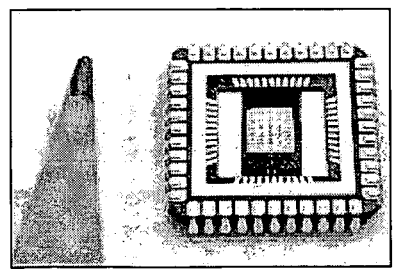

GaAs-based devices having a conducting channel with length varying from 200 to 2000 μm and a width of 200 μm were fabricated by photolithography. Each die contained 20 devices (FIG. 1E). All electrical measurements were performed with a source-measure unit (Keithley 236) on wire-bonded devices. The measurements were performed in a dark chamber with a constant flow of nitrogen that was set to a rate of 500 cc/min or, alternatively, with air as the carrier gas. No differences in the results could be found using the two different carrier gases. The different analytes were evaporated in a 30-ml chamber at room temperature and the vapors were carried by a constant nitrogen flow of 80 cc/min. This nitrogen stream was combined with the main nitrogen flow downstream and was then introduced into the sensor chamber.

Figure 10:
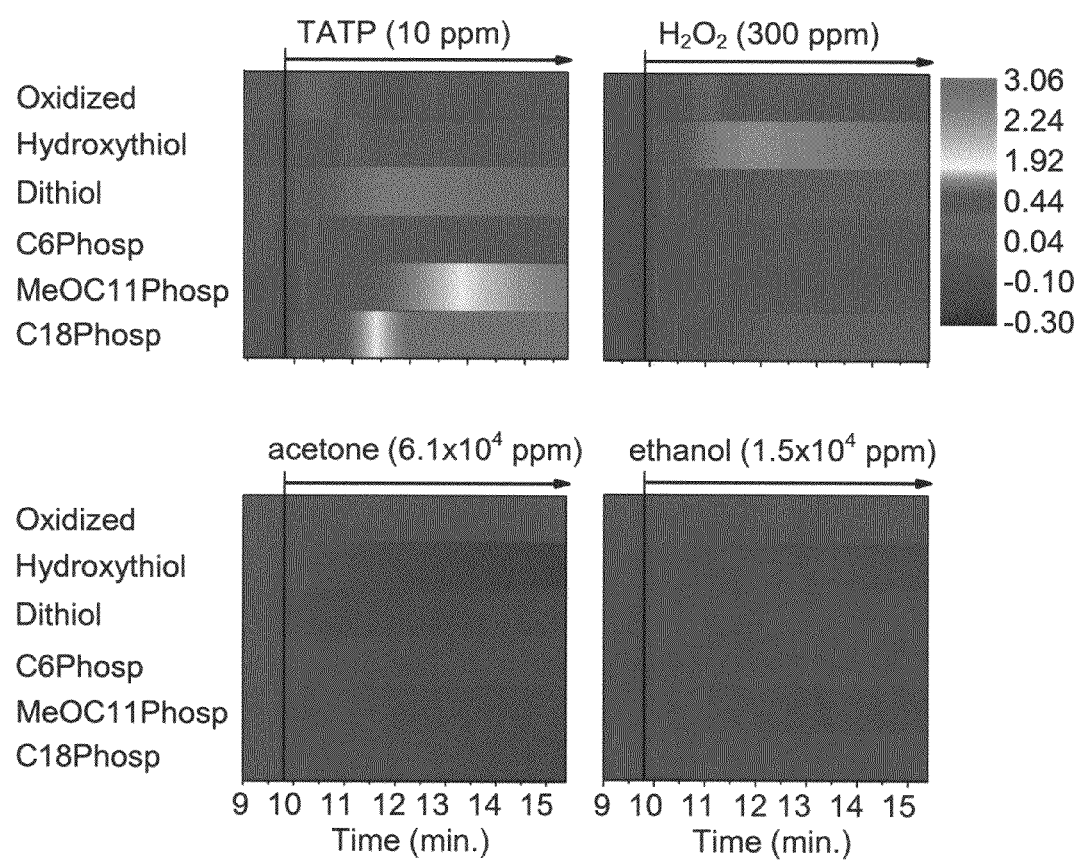
FIG. 10 shows the response $(-(I-I_0)\times 10^{-3}/I_0)$ vs. time of various GaAs-based MOCSERs, each coated with a different monolayer selected from 1-hexane-phosphonate (C6Phosp), 11-methoxyundecanephosphonate (MeOC11Phosp), 1-octadecanephosphonate (C18Phosp), 11-mercapto-1-undecanol (Hydroxythiol) or 1,9-nonane dithiol (Dithiol), as well as a bare GaAs/GaAlAs structure superficially oxidized in a controlled way using UV-activated ozone (Oxidized), upon exposure to vapors of TATP (10 ppm) (upper left panel), $H_2O_2$ (300 ppm) (upper right panel), acetone ($6.1\times 10^4$ ppm) (lower left panel) and ethanol ($1.5\times 10^4$ ppm) (lower right panel). The black line indicates the starting point of exposure to the analytes. $I_0$ is the base line current in the device, and I is the current measured following exposure to the vapor.

An array of devices was prepared, consisting of five GaAs-based devices, each coated with a different monolayer as described above, as well as a bare GaAs/GaAlAs structure that was superficially oxidized in a controlled way using UV-activated ozone (UVOCS). This oxidation process results in a reproducible oxidized surface. The array was exposed to vapors of TATP, $H_2O_2$, acetone and ethanol, and the response vs. time of each one of the devices is shown in FIG. 10. As clearly shown, using the concept of array-based sensing, we were able to distinguish between TATP and other molecules that may exist in the ambient air. In particular, whereas the elements coated with C18Phosp exhibited the strongest response to TATP, the elements coated with the thiols exhibited, in general, weaker signals. Interestingly, the oxidized element did not respond to TATP at all but responded to $H_2O_2$. All the elements did not appreciably respond to acetone and ethanol, although the concentrations of these two analytes were orders of magnitude higher than that of TATP. The response time observed depended on the diffusion time of the gases and the adsorption probability onto the layer. The actual electric response time of the sensor is several orders of magnitude faster, as can be verified by exposing it to a light pulse (Gartsman et al., 1998; Vilan et al., 1998; Wu et al., 2000; Rei Vilar et al., 2006). In addition to the analytes listed above, nine other molecules, in particular, benzonitrile, acetonitrile, benzene, mandelonitrile, m-dichlorobenzene, toluene, hexafluorobenzene, iodopentafluorobenzene and bromopentafluoro benzene, were tested; however, none of them generated any signal, except benzonitrile, for which the current in the C18Phosp-coated device increases (data not shown). This effect is opposite to that monitored for TATP with the same sensing element.

Figure 11:
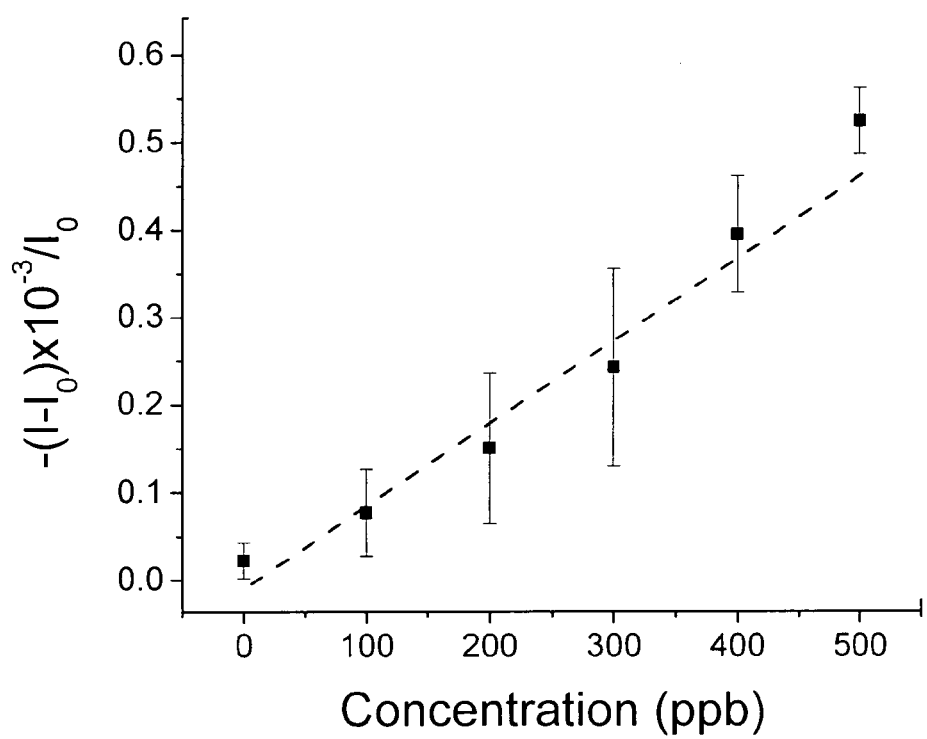
FIG. 11 shows the calibration curve of normalized responses measured for a GaAs-based MOCSER coated with 1-octadecanephosphonate (C18Phosp) upon exposure to different concentrations of TATP vapors. The response is shown as the normalized change in the current, as in FIG. 9, wherein the error bars are standard deviations obtained from four different devices.
Figure 12A:
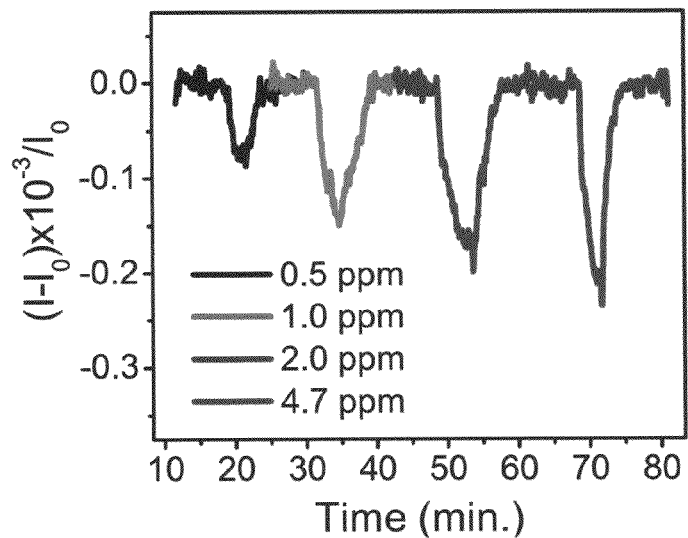
FIGS. 12A-12D show the normalized response measured for a GaAs-based MOCSER coated with 1-octadecanephosphonate (C18Phosp), when exposed to increasing concentrations of TATP (12A); the normalized response measured for said device, when exposed to increasing concentrations of TATP while constantly exposed to 40 ppm of $H_2O_2$ (12B); the calibration curve based on the data of 12A (12C); and the calibration curve based on the data of 12C (12D). The error bars are standard deviations obtained from four different devices.
Figure 12B:
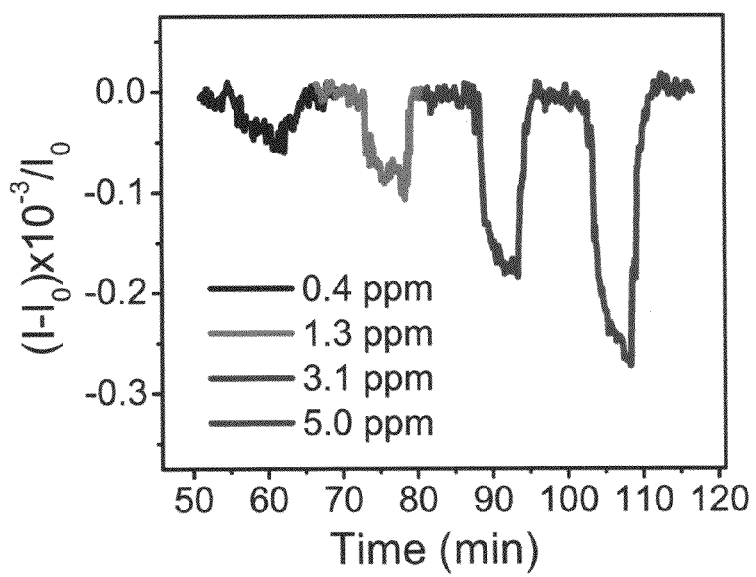
Figure 12C:
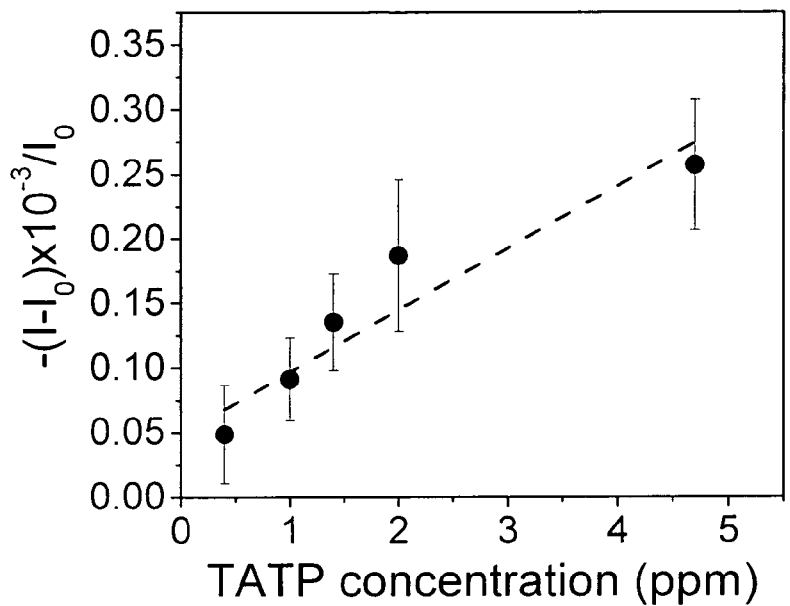
Figure 12D:
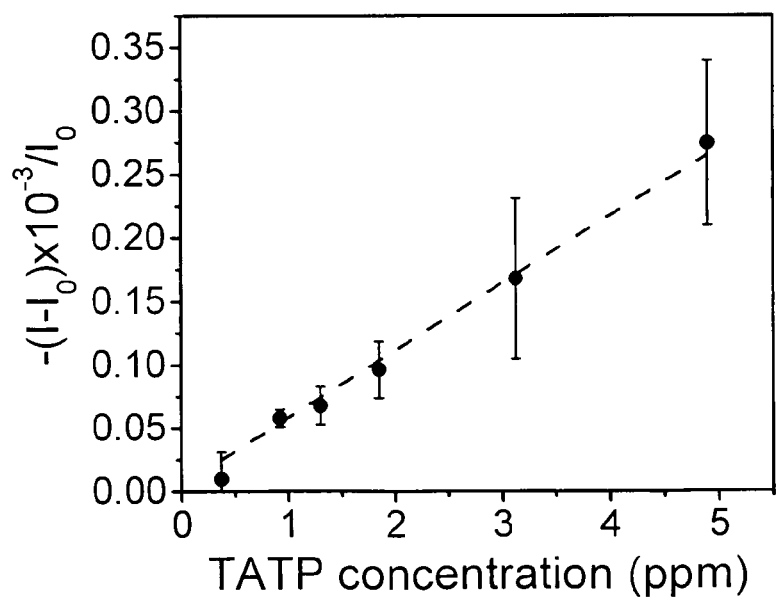

In order to test the response of the GaAs-based device coated with C18Phosp to vapors of TATP at variable concentrations, TATP was evaporated in a closed chamber and the vapors were then diluted by nitrogen. As shown in FIG. 11, the detection limit of this device was below 100 ppb of TATP, when electrical noise was the main limit to the sensitivity.

An important property of a sensor is its ability to detect the analyte in the presence of other molecules. FIG. 12A-12D show the response of the element described hereinabove to TATP, when $H_2O_2$ was either present in the measured gas or not. In comparison with the measurement shown in FIG. 11, in this experiment, TATP and $H_2O_2$ were evaporated in an open chamber and the carrier gas, i.e., nitrogen, flowed above. The concentrations reported are based on the flow rate of the carrier gas; thus providing only an approximation. As shown, the presence of $H_2O_2$ in the gas hardly interferes with the device's sensitivity towards TATP, even when the concentration of $H_2O_2$ was hundred times higher than that of the TATP.

Figure 13:
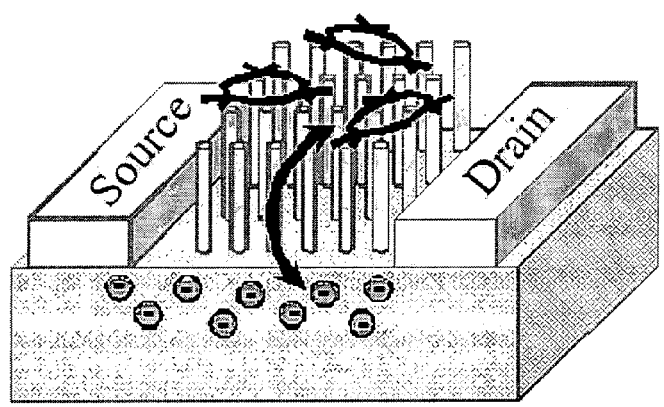
FIG. 13 shows a schematic model representing charge transfer from the substrate upon exposure to the TATP vapors.

In order to understand the mechanism by which the receptor molecules react with TATP, three different devices, each coated with C6Phosp, MeOC11Phosp or C18Phosp, were exposed to TATP, their work function was measured by monitoring the CPD using a Kelvin probe (Aqua et el., 2007) (see FIGS. 7A-7B). As found, both the response time and the amplitude of the change in the electric signal indicate the strength of the interaction between the receptor molecules and the TATP, wherein the stronger the interaction, the more efficient is the absorption of the TATP on the monolayer surface thus the faster is the response. Furthermore, CPD measurements showed that the response to TATP inversely correlate with the surface work function, i.e., with positive charging of the tail group in the monolayer. Hence, it is concluded that both sensitivity and response time correlate with and depend on the amount of positive charge at the tail of the monolayer. As the tail is more positively charged and consequently the work function is lower, the response is higher and faster. It is well established that the conductivity of alkyl chains decreases with their length, as expected in a tunnelling process (Salomon et al., 2005); however, it should be realized that the present study was not sensitive to the rate by which charge is transferred through the chain. It is enough that within the resident time, the analyte and the receptor molecules, i.e., the substrate, interact. A schematic model representing charge transfer from the substrate upon exposure to the TATP vapors is shown in FIG. 13.

When measuring the work function while the device is illuminated, it is possible to obtain information on the band bending in the semiconductor or, in other words, on the surface states. From these measurements, it is concluded that TATP efficiently interacts with the surface states in the GaAs and thereby changes the surface potential and the current going through the device. When the GaAs is oxidized, the oxide layer either eliminates the surface state or blocks its interaction with TATP, and therefore, the oxidized GaAs device does not respond to TATP.

REFERENCES

Alvarez J., Liu J., Roman E., Kaifer A. E., *Chem. Commun.*, 2000, 1151

Aqua T., Cohen H., Vilan A., Naaman R., *J. Phys. Chem. C*, 2007, 111, 16313-16318

Artzi R., Daube S. S., Cohen H., Naaman R., *Langmuir*, 2003, 19, 7392-7398

Auletta T., de Jong M. R., Mulder A., van Veggel F. C. J. M., Huskens J., Reinhoudt D. N., Zou S., Zapotoczny S., Schönherr H., Vancso G. J., Kuipers L., *J. Am. Chem. Soc.*, 2004, 126, 1577

Beulen M. W. J., Bügler J., Lammerink B., Geurts F. A. J., Biemond E. M. E. F., van Leerdam K. G. C., vanVeggel F. C. J. M., Engbersen J. F. J., Reinhoudt D. N., *Langmuir,* 1998, 14, 6424-6229

Beulen M. W. J., Bügler J., deJong M. R., Lammerink B., Huskens J., Schönherr H., Vancso G. J., Boukamp B. A., Wieder H., Offenhäuser A., Knoll W., van Veggel F. C. J. M., Reinhoudt D. N., *Chem. Eur. J.,* 2000, 6, 1176

Bohrer F. I., Colesniuc C. N., Park J., Schuller I. K., Kummel A. C., Trogler W. C., *J. Am. Chem. Soc.,* 2008, 130, 3712-3713

Cohen R., Kronik L., Shanzer A., Cahen D., Liu A., Rosenwaks Y., Lorenz J. K., Ellis A. B., *J. Am. Chem. Soc.,* 1999, 121, 10545-10553

Connors K. A., *Chem. Rev.,* 1997, 97, 1325

Cotte-Rodriguez I., Chen H., Cooks R. G., *Chem. Commun.,* 2006, 953-955

Davis M. E., Brewster M. E., *Nature Rev. Drug Discov.,* 2004, 3, 1023

Dubnikova F., Kosloff R., Zeiri Y., Karpas Z., *J. Phys. Chem. A,* 2002, 106, 4951-4956

Gartsman K., Cahen D., Kadyshevitch A., Libman J., Moav T., Naaman R., Shanzer A., Umansky V., Vilan A., *Chem. Phys. Lett.,* 1998, 283, 301-306

Laine D. F., Roske C. W., Cheng I. F., *Analytica Chimica Acta,* 2008, 608, 56-60

Liu J., Ong W., Roman E., Lynn M. J., Kaifer A. E., *J. Am. Chem. Soc.,* 1999, 121, 4304

Liu J., Mendoza S., Roman E., Lynn M. J., Xu R., Kaifer A. E., *Langmuir,* 2000, 16, 3000

Liu J., Alvarez J., Ong W., Roman E., Kaifer A. E., Peinador C., *J. Am. Chem. Soc.,* 2001a, 123, 11148

Liu J., Alvarez J., Ong W., Roman E., Kaifer A. E., *Langmuir,* 2001b, 17, 6762

Liu J., Ong W., Kaifer A. E., Peinador C., *Langmuir,* 2002, 18, 5981

Liu Y. S., Ugaz V. M., North S. W. Rogers W. J. Mannan M. S., *J. Hazardous Mat.,* 2007, 142, 662-668

Lu D., Cagan A., Rodrigo R., Munez A. A., Tangkuaram T., Wang J., *Analyst,* 2006, 131, 1279-1281

Moore D. S., *Rev. Sci. Instrument.,* 2004, 75, 2499-2512

Pacheco-Londono L., Primera O. M., Ramirez M., Ruiz O., Hernandez-Rivera S. P., *Proc. SPIE-Int. Soc. Opt. Eng.,* 2006, 620634/1-620634/8

Rei Vilar M., El Beghdadi J., Debontridder F., Naaman R., Arbel A., Ferraria A. M., Botelho do Rego A. M., *Mater. Sci. Eng. C,* 2006, 26, 253-259

Rojas M. T., Königer R., Stoddart J. F., Kaifer A. E., *J. Am. Chem. Soc.,* 1995, 117, 336-343

Saenger W., Jacob J., Gessler K., Steiner T., Hoffman D., Sanbe H., Koizumi K., Smith S. M., Tahaka T., *Chem. Rev.,* 1998, 98, 1787

Salomon A., Boecking T., Chan C. K., Amy F., Girshevitz O., Cahen D., Kahn A., *Phys. Rev. Let.,* 2005, 95, 266807

Schönherr H., Beulen M. W. J., Bügler J., Huskens J., van Veggel, F. C. J. M., Reinhoudt D. N., Vancso G. J., *J. Am. Chem. Soc.,* 2000, 122, 4963

Strimbu L., Liu J., Kaifer A. E., *Langmuir,* 2003, 19, 483

Szejtli J., *Cyclodextrins and Their Inclusion Complexes*; Académiai Kiadó: Budapest, 1982

Szejtli J., *Cyclodextrin Technology*; Kluwer Academic Publishers: Dordrecht, 1988

Szejtli J., Osa T., Eds. *Comprehensive Supramolecular Chemistry*; Elsevier: Oxford, 1996, 3

Szejtli J., *Chem. Rev.,* 1998, 98, 1743

Traversa E., de Vona M. L., Licoccia S., Sacerdoti M., Carotta M. C., Crema, L., Martinelli G., *J. Sol-Gel Sci. Tech.,* 2001, 22, 167-179

Vilan A., Ussyshkin R., Gartsman K., Cahen D., Naaman R., Shanzer A., *J. Phys. Chem. B,* 1998, 102, 3307-3309

Vilan A., Ghabboun J., Cahen D., *J. Phys. Chem. B,* 2003, 107, 6360-3676

Villalonga R., Cao R., Fragoso A., *Chem. Rev.,* 2007, 107, 3088-3116

Wu D. G., Ashkenasy G., Shvarts D., Ussyshkin R. V., Naaman R., Shanzer A., Cahen D., *Angew. Chem. Int. Ed.,* 2000, 39, 4496-4500

Zapotoczny S., Auletta T., de Jong M. R., Schönherr H., Huskens J., van Veggel F. C. J. M., Reinhoudt D. N., Vancso G. J., *Langmuir,* 2002, 18, 6988

The invention claimed is:

1. A semiconductor device for the detection of a peroxide-based explosive, said device being composed of at least one insulating or semi-insulating layer, at least one conducting semiconductor layer, two conducting pads, and a layer of multifunctional organic molecules, each one of said molecules being (i) a cyclodextrin, optionally perthiolated or perphosphonated; or (ii) a compound of the formula RPO(OH)$_2$ or RSH, wherein R is an aliphatic hydrocarbyl optionally either interrupted with one or more heteroatoms selected from the group consisting of O, S and N, or containing a functional end-group comprising a heteroatom selected from the group consisting of O, S and N, wherein said at least one conducting semiconductor layer is on top of one of said insulating or semi-insulating layers, said two conducting pads are on both sides on top of an upper layer which is either one of said conducting semiconductor layers or another of said insulating or semi-insulating layers, making electrical contact with said at least one conducting semiconductor layer, and said layer of multifunctional organic molecules is adsorbed on the surface of said upper layer, between the two conducting pads, and wherein exposure of said multifunctional organic molecules to a gaseous mixture containing vapors of said peroxide-based explosive causes a current change through the semiconductor device when a constant electric potential is applied between the two conducting pads.

2. The semiconductor device of claim 1, composed of at least one insulating or semi-insulating layer, one conducting semiconductor layer, two conducting pads, and a layer of multifunctional organic molecules, wherein said conducting semiconductor layer is on top of one of said insulating or semi-insulating layers, said two conducting pads are on both sides on top of an upper layer which is either said conducting semiconductor layer or another of said insulating or semi-insulating layers, making electrical contact with said conducting semiconductor layer, and said layer of multifunctional organic molecules is adsorbed on the surface of said upper layer, between the two conducting pads.

3. The semiconductor device of claim 1, wherein said peroxide-based explosive is triacetone triperoxide (TATP).

4. The semiconductor device of claim 1, wherein said cyclodextrin is an α-, β- or γ-cyclodextrin, optionally perthiolated or perphosphonated.

5. The semiconductor device of claim 4, wherein said cyclodextrin is a perthiolated α-, β- or γ-cyclodextrin.

6. The semiconductor device of claim 5, wherein said cyclodextrin is per-6-thio-β-cyclodextrin.

7. The semiconductor device of claim 1, wherein said cyclodextrin is in the form of an inclusion complex with a hydrophobic guest molecule capable of removing water molecules adsorbed within a conical cavity of said cyclodextrin.

8. The semiconductor device of claim 7, wherein said hydrophobic guest molecule is a cyclic hydrocarbon.

9. The semiconductor device of claim 8, wherein said cyclic hydrocarbon is adamantane.

10. The semiconductor device of claim 7, wherein said cyclodextrin is an inclusion complex of per-6-thio-β-cyclodextrin with adamantane.

11. The semiconductor device of claim 1, wherein the multifunctional organic molecule is a compound of the formula $RPO(OH)_2$ or RSH, wherein R is a linear or branched $C_2$-$C_{30}$ alkyl, optionally either interrupted with a heteroatom selected from the group consisting of O, S and N, or containing a functional end-group comprising a heteroatom selected from the group consisting of O, S and N.

12. The semiconductor device of claim 11, wherein the multifunctional organic molecule is
  (i) a compound of the formula $RPO(OH)_2$, wherein R is a linear $C_6$-$C_{22}$ alkyl, optionally either interrupted with a heteroatom selected from the group consisting of O, S and N, or containing a functional end-group comprising a heteroatom selected from the group consisting of O, S and N; or
  (ii) a compound of the formula RSH, wherein R is a linear $C_6$-$C_{22}$ alkyl, optionally either interrupted with a heteroatom selected from the group consisting of O, S and N, or containing a functional end-group comprising a heteroatom selected from the group consisting of O, S and N.

13. The semiconductor device of claim 12, wherein the multifunctional organic molecule is a compound of the formula $RPO(OH)_2$ selected from the group consisting of 1-hexanephosphonate, 9-methoxynonanephosphonate, 11-methoxyundecanephosphonate and 1-octadecanephosphonate; or a compound of the formula RSH selected from the group consisting of 11-mercapto-1-undecanol and 1,9-nonanedithiol.

14. The semiconductor device of claim 1, wherein
  (i) each one of said at least one conducting semiconductor layer is a semiconductor selected from the group consisting of a III-V and a II-VI material, and a mixture thereof, wherein III, V, II and VI denote the Periodic Table elements III=Ga, In; V=As, P; II=Cd, Zn; VI=S, Se, Te; or
  (ii) each one of said at least one insulating or semi-insulating layer is a dielectric material selected from the group consisting of silicon oxide, silicon nitride and an undoped semiconductor selected from a III-V and a II-VI material, and a mixture thereof, wherein III, V, II and VI denote the Periodic Table elements III=Ga, In; V=As, P; II=Cd, Zn; VI=S, Se, Te.

15. The semiconductor device of claim 14, wherein each one of said at least one conducting semiconductor layer is doped GaAs or doped (Al,Ga)As; or each one of said at least one insulating or semi-insulating layer is undoped GaAs or undoped (Al,Ga)As.

16. The semiconductor device of claim 1, composed of:
  (i) a first insulating layer of undoped GaAs which is on top of a second insulating layer of undoped GaAlAs, said second insulating layer is on top of a third insulaing layer of undoped GaAs which is on top of a fourth insulating layer of undoped GaAlAs, said fourth insulating layer is on top of a conducting semiconductor layer of GaAlAs which is on top of a fifth insulating layer of undoped GaAs that is on top of a sixth insulating layer of GaAs, wherein on top of said first insulating layer is a conducting semiconductor layer of GaAs on top of which is an upper conducting semiconductor layer of GaAs, and said layer of multifunctional organic molecules is adsorbed to said upper conducting semiconductor layer;
  (ii) a first insulating layer of GaAs which is on top of a second insulating layer of undoped GaAlAs, said second insulating layer is on top of a conducting semiconductor layer of GaAs which is on top of a third insulaing layer of undoped GaAlAs, said third insulating layer is on top of a fourth insulating layer of undoped InGaAs which is on top of a fifth insulating layer of undoped GaAs, said fifth insulating layer is on top of a sixth insulating layer of undoped GaAlAs/GaAs which is on top of a seventh insulating layer of undoped GaAs, said seventh insulating layer is on top of an eighth insulating layer of undoped GaAlAs which is on top of a conducting semiconductor layer of GaAlAs, said conducting semiconductor layer of GaAlAs is on top of a ninth insulating layer of undoped GaAs which is on top of a tenth insulating layer of GaAs, wherein on top of said first insulating layer is an upper conducting semiconductor layer of GaAs, and said layer of multifunctional organic molecules is adsorbed to said upper conducting semiconductor layer; or
  (iii) a first insulating layer of GaAs which is on top of a second insulating layer of undoped GaAlAs, said second insulating layer is on top of a conducting semiconductor layer of GaAs which is on top of a third insulating layer of undoped GaAlAs, said third insulating layer is on top of fourth insulating layer of undoped InGaAs which is on top of a fifth insulating layer of GaAs, wherein on top of said first insulating layer is an upper conducting semiconductor layer of GaAs, and said layer of multifunctional organic molecules is adsorbed to said upper conducting semiconductor layer.

17. An array of semiconductor devices for the selective detection of a peroxide-based explosive, comprising at least one semiconductor device for the detection of said peroxide-based explosive according to claim 1, and at least one additional semiconductor device for the detection of a contaminating species selected from the group consisting of CO, $CO_2$, $NO_2$, $O_2$, $N_2$, acetone, ethanol, water and peroxides different from said peroxide-based explosive, said additional semiconductor device being composed of at least one insulating or semi-insulating layer, at least one conducting semiconductor layer optionally oxidized, two conducting pads, and optionally a layer of multifunctional organic molecules capable of adsorbing said contaminating species,
  wherein said at least one conducting semiconductor layer is on top of one of said insulating or semi-insulating layers, said two conducting pads are on both sides on top of an upper layer which is either one of said conducting semiconductor layers or another of said insulating or semi-insulating layers, making electrical contact with said at least one conducting semiconductor layer, and said layer of multifunctional organic molecules, if present, is adsorbed on the surface of said upper layer, between the two conducting pads, and
  wherein exposure of said upper layer to which said layer of multifunctional organic molecules is optionally adsorbed to a gaseous mixture containing vapors of said contaminating species causes a current change through the additional semiconductor device when a constant electric potential is applied between the two conducting pads.

18. The array of semiconductor devices of claim 17, wherein said at least one additional semiconductor device is composed of at least one insulating or semi-insulating layer, one conducting semiconductor layer optionally oxidized, two conducting pads, and optionally a layer of multifunctional organic molecules capable of adsorbing said contaminating species, wherein said conducting semiconductor layer is on top of one of said insulating or semi-insulating layers, said two conducting pads are on both sides on top of an upper layer which is either said conducting semiconductor layer or another of said insulating or semi-insulating layers, making electrical contact with said conducting semiconductor layer, and said layer of multifunctional organic molecules, if present, is adsorbed on the surface of said upper layer, between the two conducting pads.

19. The array of semiconductor devices of claim 17, wherein said peroxide-based explosive is TATP.

20. The array of semiconductor devices of claim 19, wherein said at least one additional semiconductor device is composed of:

(i) at least one insulating or semi-insulating layer, an oxidized conducting semiconductor layer and two conducting pads, wherein exposure of said oxidized conducting semiconductor layer to a gaseous mixture containing vapors of a peroxide different from said peroxide-based explosive causes a current change through the additional semiconductor device when a constant electric potential is applied between the two conducting pads; or (ii) at least one insulating or semi-insulating layer, a conducting semiconductor layer, two conducting pads and a layer of multifunctional organic molecules capable of adsorbing said contaminating species, wherein exposure of said multifunctional organic molecules to a gaseous mixture containing vapors of said contaminating species causes a current change through the additional semiconductor device when a constant electric potential is applied between the two conducting pads.

21. A method for the selective detection of vapors of a peroxide-based explosive in a gaseous mixture, said method comprising:

(i) exposing an array of semiconductor devices according to claim 17 to said gaseous mixture; and monitoring the presence of said peroxide-based explosive vapors in said gaseous mixture according to the changes in the current measured in said at least one semiconductor device for the detection of said peroxide-based explosive vapors and said at least one additional semiconductor device for the detection of said contaminating species when a constant electric potential is applied between the two conducting pads of each one of said devices.

* * * * *